United States Patent
Samadpour

(10) Patent No.: US 11,320,342 B2
(45) Date of Patent: May 3, 2022

(54) APPARATUS FOR SAMPLING SURFACES

(71) Applicant: Institute for Environmental Health, Inc., Lake Forest Park, WA (US)

(72) Inventor: Mansour Samadpour, Lake Forest Park, WA (US)

(73) Assignee: Institute for Environmental Health, Inc., Lake Forest Park, WA (US)

( * ) Notice: Subject to any disclaimer, the term of this patent is extended or adjusted under 35 U.S.C. 154(b) by 45 days.

(21) Appl. No.: 15/957,804

(22) Filed: Apr. 19, 2018

(65) Prior Publication Data

US 2018/0306678 A1   Oct. 25, 2018

Related U.S. Application Data

(60) Provisional application No. 62/487,966, filed on Apr. 20, 2017, provisional application No. 62/599,625, filed on Dec. 15, 2017.

(51) Int. Cl.
*G01N 1/02* (2006.01)
*G01N 1/10* (2006.01)
(Continued)

(52) U.S. Cl.
CPC ............... *G01N 1/02* (2013.01); *A61F 13/56* (2013.01); *C12M 33/02* (2013.01); *G01N 1/10* (2013.01);
(Continued)

(58) Field of Classification Search
CPC   G01N 1/02; G01N 1/10; G01N 1/286; G01N 1/2214
See application file for complete search history.

(56) References Cited

U.S. PATENT DOCUMENTS 3,058,139 A * 10/1962 Dryden ................. A47K 7/028
                                                        15/244.1
4,175,439 A * 11/1979 Laker ................... A61B 10/007
                                                        422/944

(Continued)

FOREIGN PATENT DOCUMENTS

| CA | 2757811 A1 | 5/2013 |
|----|------------|--------|
| GB | 2421186 A | 6/2006 |
| WO | 2007/093009 A1 | 8/2007 |

OTHER PUBLICATIONS

International Search Report and Written Opinion dated Jul. 19, 2018, issued in International Patent Application No. PCT/US2018/028441, filed Apr. 19, 2018, 17 pages.

*Primary Examiner* — Helen C Kwok
(74) *Attorney, Agent, or Firm* — Barry L. Davison; Davis Wright Tremaine LLP

(57) ABSTRACT

Disclosed are devices and methods using the devices for collecting biological and other specimens or substances from surfaces being interrogated for such contamination. Particular device aspects comprise a handle, with a frame at one end receptive to insertion and removal of a sampling medium (collecting member) intended for wiping against a surface, with the sampling member being held in place by passive projections from the frame without the need for the use of glue or articulating or moving parts. The Frame and/or the collecting member may also comprise at least one attached or integral scraping member or surface for breaking biofilms and thus making the microbes or other substances more available to being sampled by the collecting member.

19 Claims, 22 Drawing Sheets

(51) Int. Cl.
  *C12M 1/30* (2006.01)
  *G01N 1/28* (2006.01)
  *A61F 13/56* (2006.01)

(52) U.S. Cl.
  CPC ....... *G01N 1/286* (2013.01); *G01N 2001/028* (2013.01); *G01N 2001/2826* (2013.01)

(56) References Cited

U.S. PATENT DOCUMENTS

| | | | |
|---|---|---|---|
| 5,295,952 A * | 3/1994 | Pietrafitta | A61B 10/04 604/1 |
| 5,420,018 A * | 5/1995 | Ricci | C12M 23/22 435/287.9 |
| 5,859,375 A * | 1/1999 | Danylewych-May | G01N 1/02 73/863.21 |
| 6,423,550 B1 * | 7/2002 | Jenkins | B01L 3/505 436/518 |
| 6,446,514 B1 * | 9/2002 | Danylewych-May | G01N 1/02 73/863.12 |
| 2004/0126281 A1 * | 7/2004 | Morrison | B01L 3/545 422/400 |
| 2007/0186365 A1 | 8/2007 | Armaly, Jr. | |
| 2007/0249961 A1 * | 10/2007 | Morrison | A61B 10/0045 600/572 |
| 2013/0118275 A1 * | 5/2013 | Lafond | B25B 9/00 73/864.71 |

\* cited by examiner

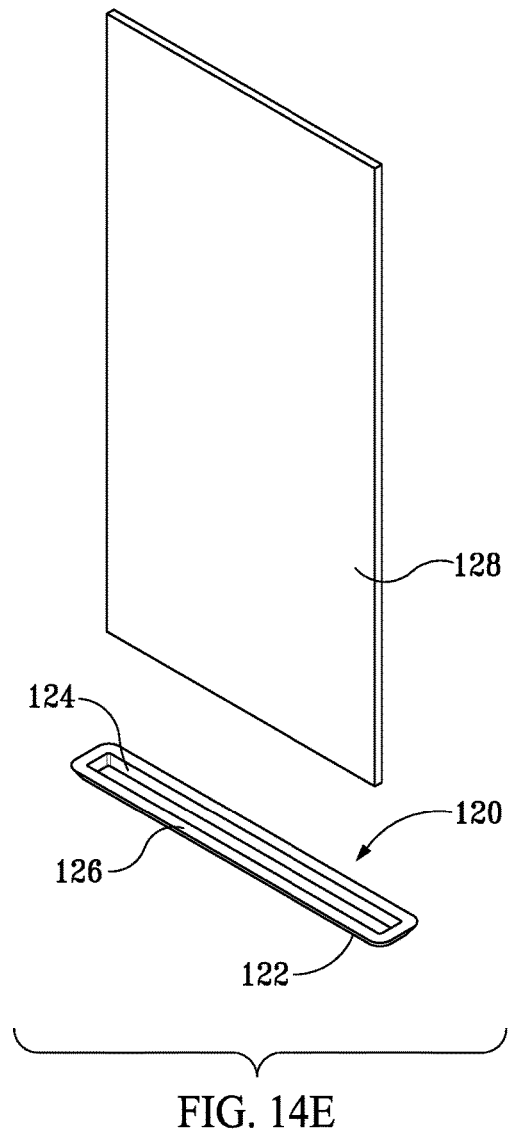
FIG. 14E
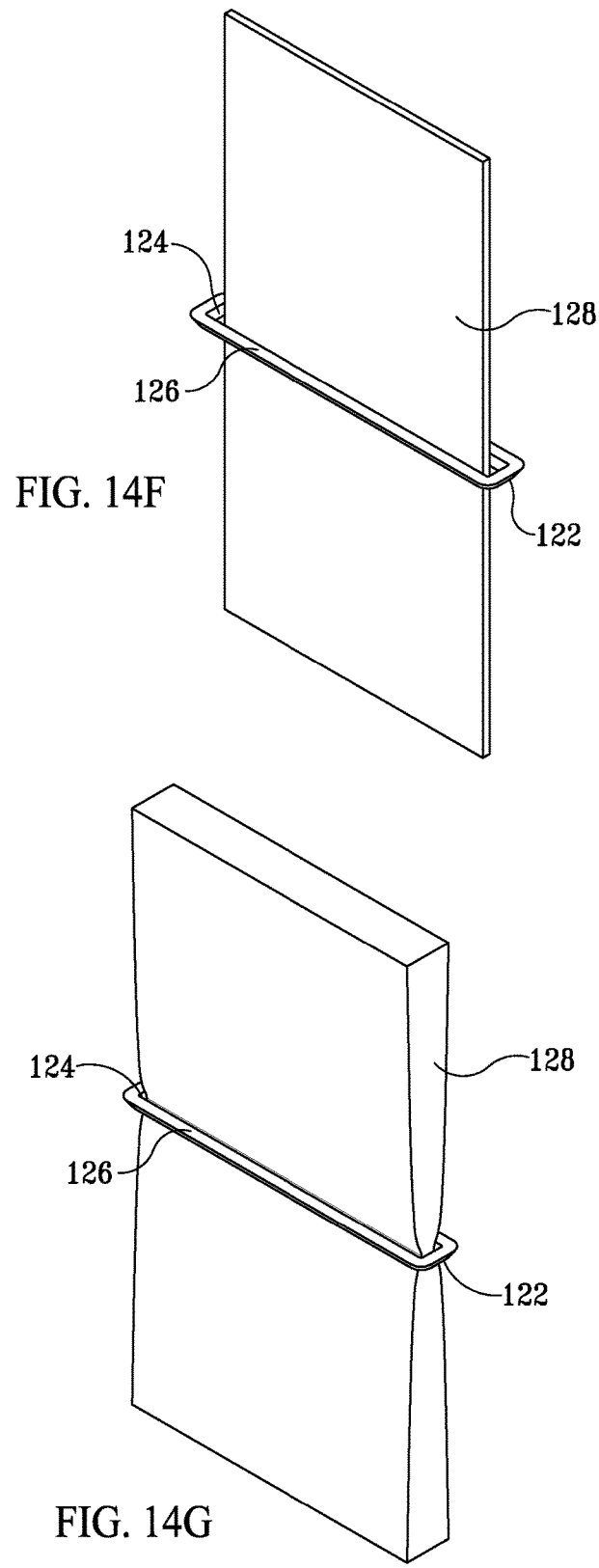
FIG. 14F
FIG. 14G

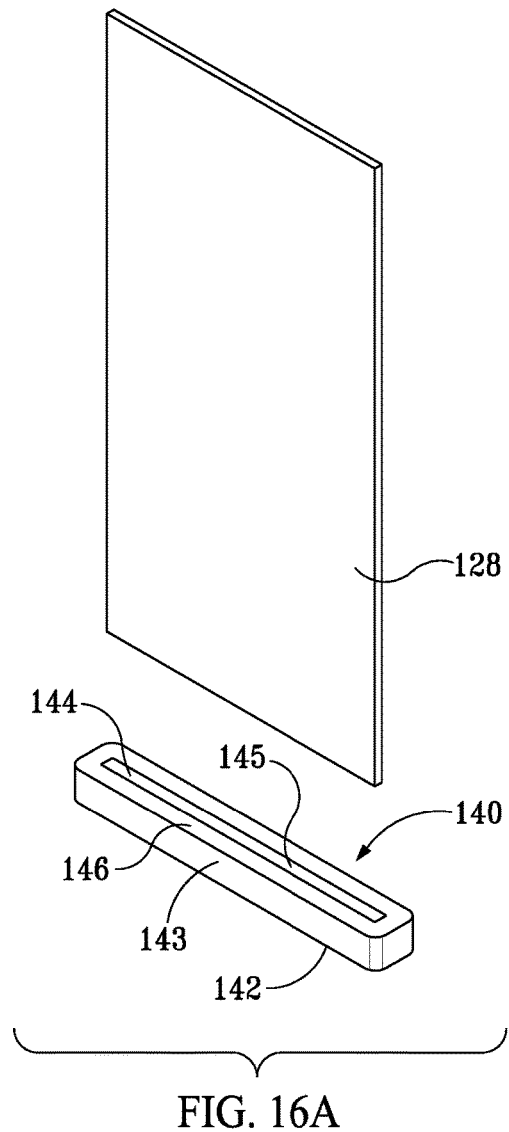
FIG. 16A
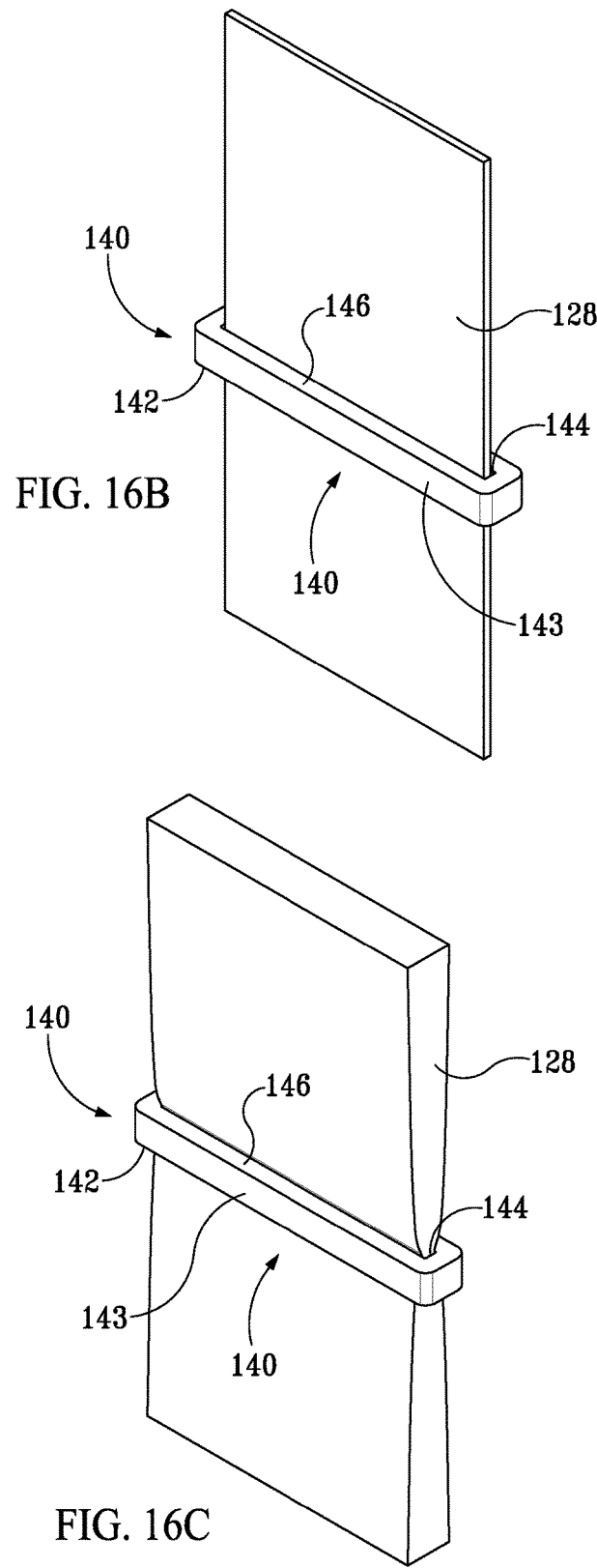
FIG. 16B
FIG. 16C

APPARATUS FOR SAMPLING SURFACES

CROSS REFERENCES TO RELATED APPLICATIONS

This application claims the benefit of U.S. Provisional Patent Application No. 62/487,966, filed Apr. 20, 2017, and claims the benefit of U.S. Provisional Patent Application No. 62/599,625, filed Dec. 15, 2017, the disclosures of which are herein incorporated by reference in their entirety.

FIELD OF THE INVENTION

Aspects of the present invention relate generally to devices for sampling surfaces, and in more particular aspects relate to collecting biological specimens (e.g., bacteria, pathogens, indicator organisms, or other microbes, etc.) and other substances and specimens (e.g., toxins, heavy metals, allergens, etc.) from surfaces. Additional aspects relate to collection members mountable to the disclosed devices, and methods of sampling using same.

BACKGROUND

Industrial processes generally must be monitored and maintained to prevent conditions of adverse exposure to contaminants and other substances. For example, industrial processes for the production of food and other products must be maintained in sanitary conditions to prevent microbial and chemical contamination that could expose consumers to food-borne disease and other adverse impacts. An example is a food production facility which must be operated so as to avoid contamination of food products with harmful bacteria, such as *Listeria monocytogenes, Salmonella, E. coli,* and other pathogens and microbes.

Such industrial plants have many surfaces which come into contact with the product being processed. Such surfaces are known as product contact surfaces, or also referred to as "zone 1" surfaces. Surfaces that are close to product contact surfaces known as "zone 2" surfaces. Surfaces which are away from product contact surfaces but are in the same area are called "zone 3" surfaces, and surfaces in other areas in the production facility where there is no zone 1 in the area are called "zone 4" surfaces.

Other surfaces in the plant, such as walls or floors, may also become contaminated due to, e.g., splatterings and drippings emanating from the product. All of these surfaces may thus become covered with nutrient-containing liquids and particles that are conducive to the growth of, e.g., pathogenic bacteria or other microbes, which bacteria or other microbes may eventually make their way back into the stream of product that will eventually be delivered to consumers.

Accordingly, if the plant is to produce wholesome product, measures must be taken to keep all of these surfaces clean, by regular washing and other means of decontamination. To measure and document that the cleaning/decontamination has been done properly and effectively, the surfaces are wiped with swabs or sponges that can collect and absorb stray bacteria or other microbes remaining on the surface. These swabs or sponges, along with any absorbed bacteria or other microbes, are collected and tested (e.g., at a testing laboratory) for the presence of the absorbed bacteria, pathogens, indicator organisms, or other microbes on them, so that an estimate of the amount of any surface contamination may be obtained. Such samples can also be collected for chemical and biological analysis such as testing for toxins, heavy metals, allergens, etc.

The current state of the art for surface sampling is represented by a device containing a handle and detachable tip to which a suitable sampling medium such as sponge, polyurethane, microfiber fabric and the like is glued. Typical surface areas of such so-called "sponge sampling devices" are about is 1×3 inches (distinguishable from the much smaller surface areas of "swab sampling devices" or "swab samplers"). While the sampling medium (e.g., sponge, polyurethane, microfiber fabric and the like) has a front and a back surface, since one side is glued to the sampler's detachable tip the total area for sampling is 3 square inches.

As the regulatory pressure for maintaining a sanitary environment during food, nutraceutical and pharmaceutical production has increased over the last decade, the surface area that is sampled at each sampled site has grown from 2×2 inches to 12×12 inches. Yet, the same devices with 3 square inches of sampling medium surface area are used to collect a surface sample 36 times larger than previously envisioned. There may be a risk in the industry that the typical 1×3 inch sponge does not have enough surface area to allow for effective sampling of the larger size sampling sites that are now required. An improved sampling device offering more surface area sampling capability may provide great benefits and reduce risk of missing contamination during sampling.

Another potential problem is that microbes of interest may be attached to surfaces through bio-films (e.g., microbes adhered to each other within a self-produced matrix of extracellular polymeric substance (EPS) or polymeric conglomeration generally composed of extracellular DNA, proteins, and polysaccharides). Bio-films are tough and cannot be reliably removed or sampled with soft absorbent sampling media such as cellulose, sponge, polyurethane, microfibers, and the like. There is thus a need for a sampling device which can efficiently scrape or disrupt bio-films from a surface, while in addition contacting the surface with a soft, absorbent sponge.

SUMMARY OF THE INVENTION

As a solution to these problems, aspects of the invention use frictional retention to avoid the use of glue or other means which permanently affix one face or side of an absorbent sampling media (e.g., a rectangular sponge having upper and lower faces, and end and side faces) to the handle and/or frame. Thus, in particular disclosed embodiments, no part of the sampling media, or only a limited portion thereof, is occluded from contact with surfaces due to glue or other means for affixing the sampling media to the handle and/or frame. Rather, in preferred aspects, both faces or substantially both faces, of the sampling media are available for wiping over the surface to be sampled, resulting in much more surface available for adsorption of material on the surface (e.g., contamination, etc.).

In addition, the sampling media, not being glued in place, is easily detached from the handle, for example, even while it is inside a sterile plastic sampling bag. Thus, the sampling media may remain in a sampling bag, and the handle removed, by simple application of hand-pressure applied from without the bag. The sampling media within the bag can be grasped with fingers outside of the bag, and held firmly, while the handle is withdrawn using the other hand. Thus, the sampling media is left in the bag, the handle is withdrawn, and the bag can then be sealed, ready for transport to the laboratory.

Particular embodiments provide a device for swabbing a surface and collecting a substance therefrom, comprising a handle, a frame connected to said handle, and a collecting member (e.g., sponge or other absorbent sampling media) releasably mounted to said frame, optimally said collecting member comprising material (e.g., sponge or other absorbent material) which undergoes expansion upon absorption of liquid, wherein such expansion results in a force tending to retain said collecting member within said frame.

In particular aspects, said collecting member comprises sampling media selected from the group including the following: sponge, polyurethane, cotton, cellulose, and microfiber.

In particular aspects, the frame comprises tines and at least one cross-brace member (e.g., a scraper member extending between the tines and configured to disrupt or dislodge biofilm).

In particular embodiments, a scraper member is attached to at least one face, end or side of the collecting member (e.g., a rectangular sponge or the like), and the collecting member with the attached scraper member(s) is, in operation of the device, releasably mounted to the frame, which may or may not have a cross-brace member/scraper.

In particular aspects, the cross-brace member of the frame, and/or of a scraper member attached to a collecting member mounted in a frame (e.g., without a frame cross-brace member), is positioned so that scraping may occur with the surface being sampled, so that biofilm may be disrupted.

Particular aspects provide a device for swabbing a surface and collecting a sub-stance therefrom, comprising a handle and a collecting member (e.g., sponge or other absorbent media) releasably mounted to the handle, the handle including at least one gripping member adapted to exert force against the collecting member when said collecting member is exposed to liquid.

Particular aspects provide devices for swabbing a surface and collecting a substance therefrom, comprising: a handle having a user gripping portion or end and a frame end; a frame connected to or integral with the handle at the frame end and having upper and lower frame surfaces, the frame defining a framed or partially framed area; and one or more cantilever retention members positioned on each of the upper and lower frame surfaces, and extending at least partially over the framed or partially framed area, wherein the frame and cantilever retention members are configured to cooperatively receive and frictionally retain, in operation of the device, a releasably mountable collecting member between the upper and lower cantilever retention members within the framed or partially framed area. In the devices, the frame may be integral with the handle, and/or the cantilever members may be integral with the frame. In the devices, the handle and frame may be coplanar or substantially coplanar. In the devices, the handle and frame may each be planar or substantially planar, and the respective planes may have an offset angle. In the devices, the frame may be circular or substantially circular. In the devices, the frame may be rectangular or substantially rectangular with at least two sides and open at the end distal to the user gripping portion, to facilitate, in operation of the device, receipt of a collecting member. In the devices, the frame may comprise two tines extending from the frame end of the handle, and each tine may have one or more of the cantilever retention members configured, in operation of the device, to receive and frictionally retain a collecting member. The devices may further comprise at least one cross-brace member extending between and/or connecting the tines. In the devices, each tine may be split or divided into an upper split tine portion and a lower split tine portion to provide the cantilever retention members and configured, in operation of the device, to receive and frictionally retain a collecting member. In the devices, the cross-brace member may be positioned and configured to provide for scraping of a surface being sampled, to disrupt biofilm or other surface substance during sampling. The devices may further comprise a mounted and/or frictionally retained collecting member. In the devices, the collecting member may comprise an expandable collecting material or medium that undergoes expansion upon absorption of liquid, and wherein the frame and cantilever retention members may be configured to receive and retain the expandable collecting material or medium by pinching or gripping pressure after absorption of the liquid. In the devices, the collecting member may comprise a non-expandable or substantially non-expandable base element or plate attached to or integral with collecting material or medium that undergoes expansion upon absorption of liquid, and wherein the frame and cantilever members may be configured to frictionally retain a portion of the non-expandable or substantially non-expandable base element or plate. In the devices, the non-expandable or substantially non-expandable base element or plate may comprise protrusions or other structures that cooperatively contact the frame and/or the cantilever members to provide friction or stability for retaining the collecting member. In the devices, the collecting material or medium that undergoes expansion upon absorption of liquid may comprise at least one sampling medium selected from the group consisting of: sponge, polyurethane, cotton, cellulose, and microfiber.

Additional aspects provide collecting members, including for use with the devices disclosed herein. For example, particular aspects provide collecting members for sampling a surface, comprising a non-expandable or substantially non-expandable base element or plate having upper and lower surfaces and an edge, the base element or plate attached to or integral with a collecting material that undergoes expansion upon absorption of liquid, the collecting material sized to cover a majority portion of the upper and lower surfaces of the base element or plate, and folded over the edge thereof. In the collecting members, the base element or plate may comprise a rectangle or square, having a depth substantially less than its width and/or length, having upper and lower surfaces to which the collecting material is attached, and four sides or edges comprising the edge covered by the folded-over collecting material, an opposite edge free of collecting material, and two side edges. In the collecting members, a portion of the upper and/or lower surface may either be free of the collecting material and/or may not be attached to the collecting material, to provide, in operation of the collecting member, an accessible surface area for mounting the collecting member to a receiving frame of a sampling device. In the collecting members, the accessible surface area may comprise one or more slot-shaped portions of the upper and lower surfaces. In the collecting members, the collecting material that undergoes expansion upon absorption of liquid, or a portion thereof, may be configured to have a narrow, v-shaped, a right angled, conical or pointed portion to facilitate surface sampling access in tight or restricted areas of a surface. The collecting members may further comprise protrusions or other structures on the accessible surface area configured, in operation of the collecting member, to provide friction or stability for retaining the collecting member to a frame. The collecting members may further comprise a scraper member configured, in operation of the device, for contacting a surface to be sampled. In the collecting members, the scraper member may comprise a scraper band formed of a resilient material and having an outer and an inner surface, the inner surface forming a slot configured to retain the collecting member, and the outer surface comprising a scraping edge configured, in operation of the device, for contacting and scraping a surface to be sampled. In the collecting members, the collecting material may be retained in the slot by pinching pressure or compression between portions of the inner surface of the scraper band. In the collecting members, the outer surface of the scraper band may be planar or substantially planar. In the collecting members, the outer surface of the scraper band may comprise one or more substantially planar portions configured to extend away from, or extend at an outward angle away from the collecting member to provide the scraping edge. In the collecting members, the outer surface of the scraper band may comprise one or more raised portions to provide the scraping edge. The collecting members may further comprise a handle with a user gripping portion, and the handle may be attached to a frame portion configured to retain the collecting member, to provide a sampling device for swabbing a surface and collecting a substance therefrom.

Yet additional aspects provide collecting members, including for use with the devices disclosed herein. For example, particular aspects provide collecting members for sampling a surface, comprising: a collecting member comprising a material that undergoes expansion upon absorption of a liquid; and a scraper band formed of a resilient material and having an outer and an inner surface, the inner surface forming a slot configured to retain the collecting member, and the outer surface comprising a scraping edge configured, in operation of the device, for contacting and scraping a surface to be sampled. In the collecting members, the material that undergoes expansion upon absorption of a liquid (collecting material) may be retained in the slot by pinching pressure/compression between portions of the inner surface of the scraper band. In the collecting members, the outer surface of the scraper band may comprise one or more planar or substantially planar portions. In the collecting members, the outer surface of the scraper band may comprise one or more planar or substantially planar portions configured to extend away from, or extend at an outward angle away from the collecting member to provide the scraping edge. In the collecting members, the outer surface of the scraper band may comprises one or more raised portions to provide the scraping edge. The collecting members may further comprise a handle with a user gripping portion, the handle may be attached to a frame portion configured to retain the collecting member, to provide a sampling device for swabbing a surface and collecting a substance therefrom.

Further aspects provide devices for swabbing a surface and collecting a substance therefrom, comprising a handle having a slot or receiving channel defined by surfaces of the handle, the internal surfaces of the slot or receiving channel configured to cooperatively receive and frictionally retain, in operation of the device, a collection member insertable into or through the slot or receiving channel. The devices may further comprise a mounted and/or frictionally retained collecting member. In the devices, the collecting member may comprise material which undergoes expansion upon absorption of liquid, and wherein the internal surfaces of the slot or receiving member may be configured to receive and frictionally retain the collecting member or the expanded collecting member after absorption of the liquid. The devices may further comprise at least one scraping member, positioned on the outer surface of the handle portion, and configured to provide for scraping of a surface being sampled, to disrupt biofilm or other surface substance during sampling. In the devices, the scraping member may be positioned on the outer surface of the handle at or near the slot.

Yet further aspects provide devices for swabbing a surface and collecting a substance therefrom, comprising: a handle having a user gripping portion or end and a frame end; and a frame connected to or integral with the handle at the frame end and having upper and lower surfaces and two tines extending in a direction away from the frame, and wherein each tine is longitudinally split or divided into upper and lower portions, and configured to receive and frictionally retain, in operation of the device, a portion of a collecting member between the upper and lower portions of the split tines. The devices may further comprise a mounted and/or frictionally retained collecting member according to any of the collecting members described herein.

Still further aspects provide methods for swabbing a surface and collecting a substance therefrom, comprising; swabbing a surface and collecting a substance therefrom, using any of the sampling devices and/or the collecting members described herein. In the methods, the substance may be at least one selected from biological specimens, microbes, bacteria, pathogens, indicator organisms, toxins, heavy metals, DNA, proteins, polysaccharides, and allergens.

BRIEF DESCRIPTION OF THE DRAWINGS

FIGS. 14A-14G show an additional exemplary collecting member embodiment of the invention, wherein the collecting member has an attached (or is combined with a) scraper band.

FIGS. 16A-16C show an additional exemplary collecting member embodiment of the invention, wherein the collecting member has an attached (or is combined with a) scraper band.

DETAILED DESCRIPTION OF THE INVENTION

Figure 1:
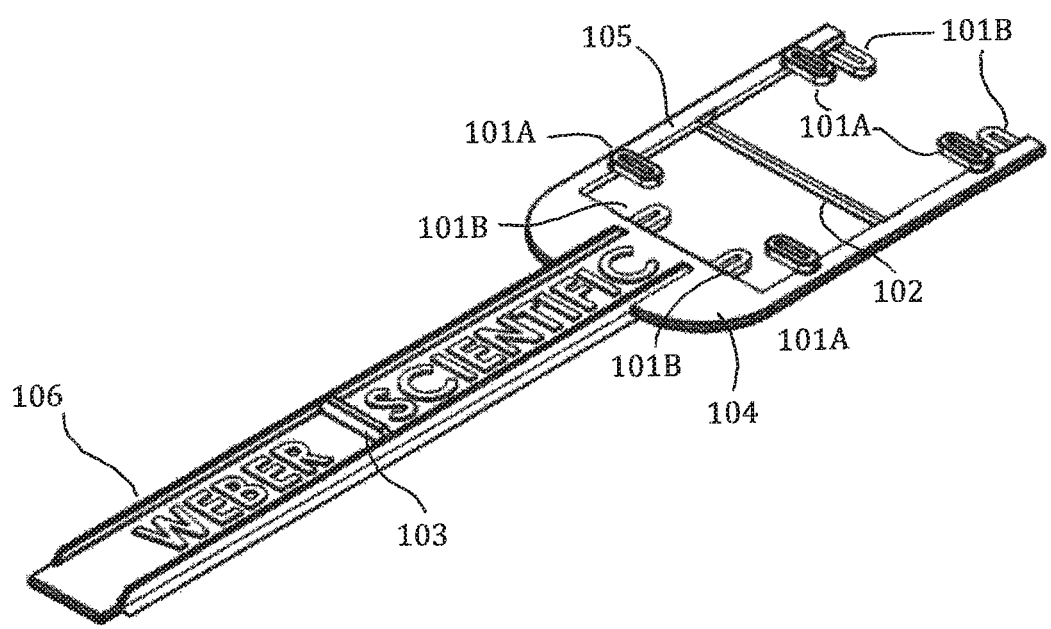
FIG. 1 is an upper perspective view of an exemplary embodiment of the present invention.

To achieve aspects of this invention, there is provided a device for swabbing a surface and collecting one or more substances (e.g., bacterial or other microbes, toxins, heavy metals, allergens, etc.) therefrom, the device comprising a handle and a frame member attached to, or integral with said handle, which frame is adapted for receiving a sample collecting member comprising materials which, in particular aspects, expand upon hydration, said frame comprising one or more retaining members which exert force upon said sample collecting member, e.g., when it is in hydrated form.

In particular embodiments, the sample collecting member is inserted into said frame when it is in non-hydrated form, and thus smaller in size. This smaller size permits it to slide easily into the frame member. Thereafter, hydration of said collecting member causes it to expand and exert force against the retaining members, which force tends to fix said sample collecting member into place. This places the device into condition so that the hydrated sample collecting member may be swabbed upon a surface. During swabbing, opposing surfaces of the collecting member are available for application to a surface being sampled, in contrast to some prior art devices wherein some surfaces were made not available due to the need to glue the collecting member to a handle.

In additional aspects, the sample collecting member comprises a sample collecting material element attached (e.g., adhesive, stapled, pinned, etc., or integral) to a non-expandable or substantially non-exapandable base element, which base element or portion(s) thereof is reversibly slidable/insertable into the frame member and sized/configured to provide sufficient frictional contact with the frame to retain the sample collecting member. In particular aspects, the frame and/or cantilever members are configured, in operation of the device, to frictionally retain a non-expandable or substantially non-expandable portion of a collecting member having a non-expandable base element attached to or integral with collecting material that undergoes expansion upon absorption of liquid.

Certain principles of operation of the disclosed devices are as follows: The handle of the device is adapted for holding by a human hand or a mechanical or robotic device suitable to achieve an equivalent result. The handle is provided with (e.g., joined/attached to, integral to, etc.) a frame to which a collecting member may be connected. Said collecting member comprises a material which absorbs liquid and expands upon the absorption of the liquid. The collecting member may be non-flexible when liquid is not present, but preferably is at least somewhat flexible after it has absorbed water. The frame and collecting member are arranged such that expansion of the collecting member upon liquid adsorption tends to exert a friction force upon said frame. This friction force, in the configuration of the frame, is sufficient to hold/retain the absorbing member in a fixed or substantially fixed relationship to the frame during a swabbing operation. However, where the collecting member is flexible after it has absorbed liquid, the friction force holding the absorbing member against the frame may be overcome by another force, such as gripping and pulling with a user's fingers, allowing the absorbing member to be easily removed from the frame.

Referring to the exemplary embodiment of FIG. 1, the device comprises handle 106, attached to holding frame 104. Frame 104 comprises two tines 105, cross-brace 102, and sponge-retention cantilevers 101A and 101B. In the embodiment of FIG. 1 the four cantilevers 101A are fixed to the upper surface of the tines 105, and the cantilevers 101B are fixed to the lower surface.

Figure 2:
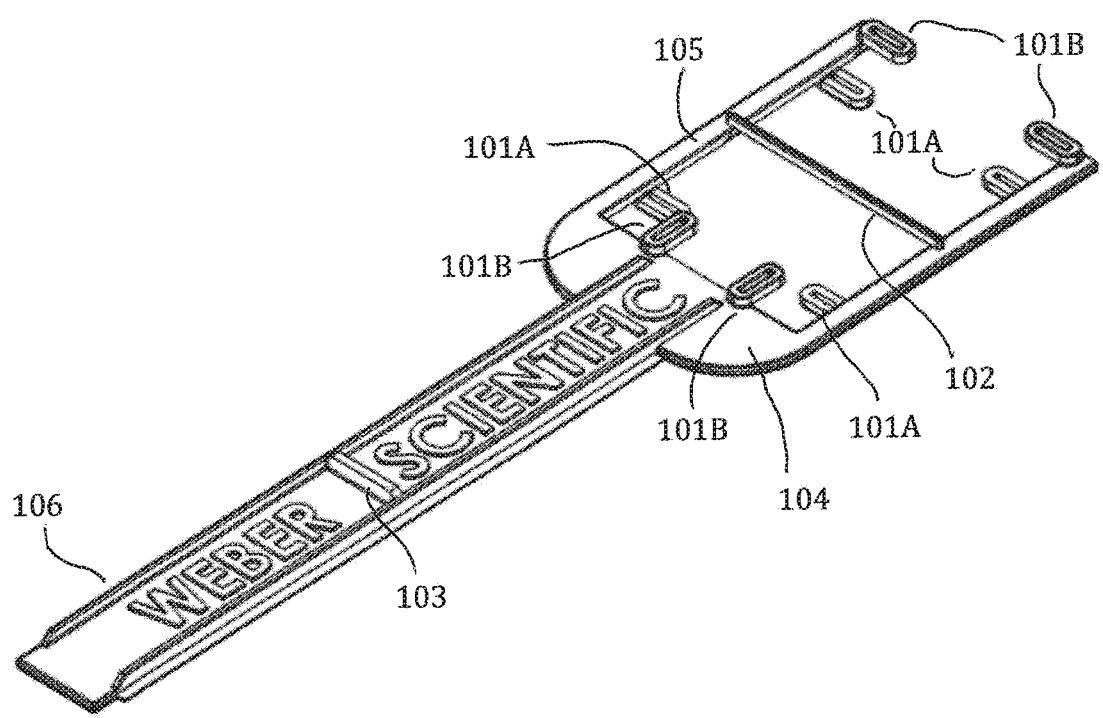
FIG. 2 is a bottom perspective view of the exemplary embodiment of FIG. 1.

FIG. 2 shows the same embodiment as FIG. 1, except now the perspective is flipped upside down, so that the lower surface of frame 104 is upwards. It can be seen that the gripping member cantilevers 101A and 101B occupy parallel planes that are separated from one another by a distance equal to the thickness of tines 105.

In both FIG. 1 and FIG. 2 there is shown thumb guard 103, which acts as a structural brace and also as a place where a user's thumb may rest when handle 106 is grasped by a user's hand while in use.

Optionally, three X-shaped structural braces (not shown), are included in (e.g., integral with) the handle 106 to provide handle 106 with additional stiffness, thus preventing unwanted twisting of the handle during use. In an alternative embodiment, handle 106 could simply be made thicker, albeit at the cost of additional material.

Figure 3:
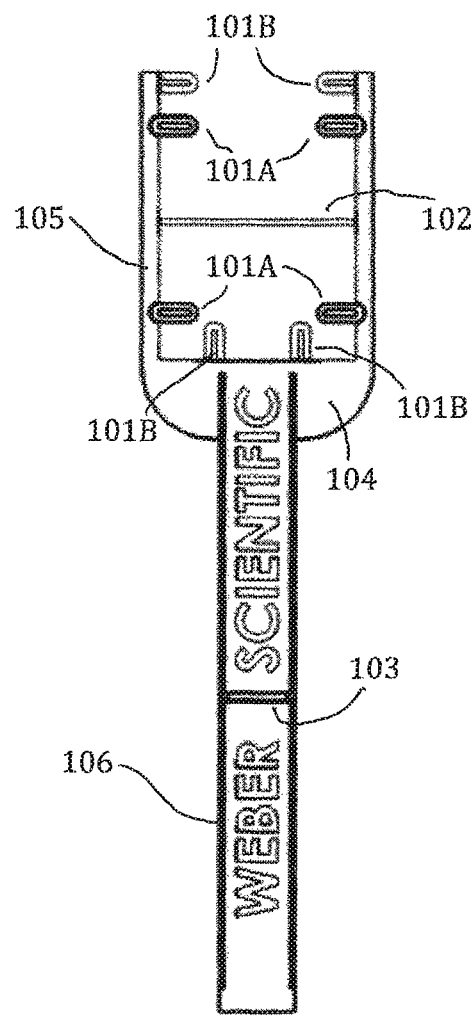
FIG. 3 is a top view of the exemplary embodiment of FIG. 1.

FIG. 3 is a top view of the embodiment shown in FIGS. 1 and 2.

Figure 4:
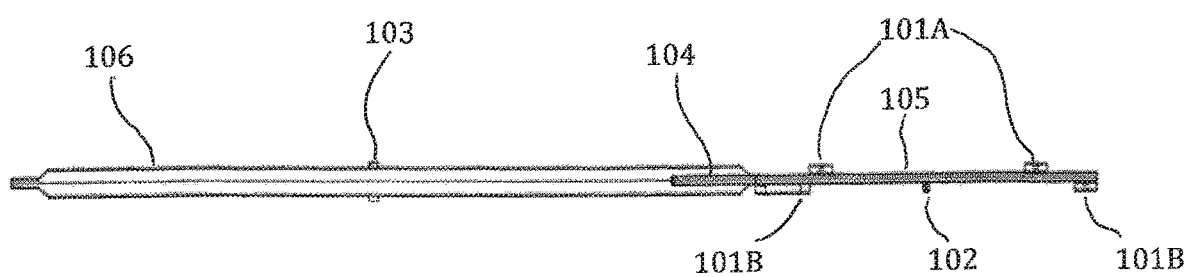
FIG. 4 is a side view of the exemplary embodiment of FIG. 1.

FIG. 4 is a side view of the embodiment shown in FIGS. 1 and 2. In this view it can be seen that cantilever members 101A and 101B are located in different planes, affixed to the upper and lower surfaces of tines 105.

Figure 5A:
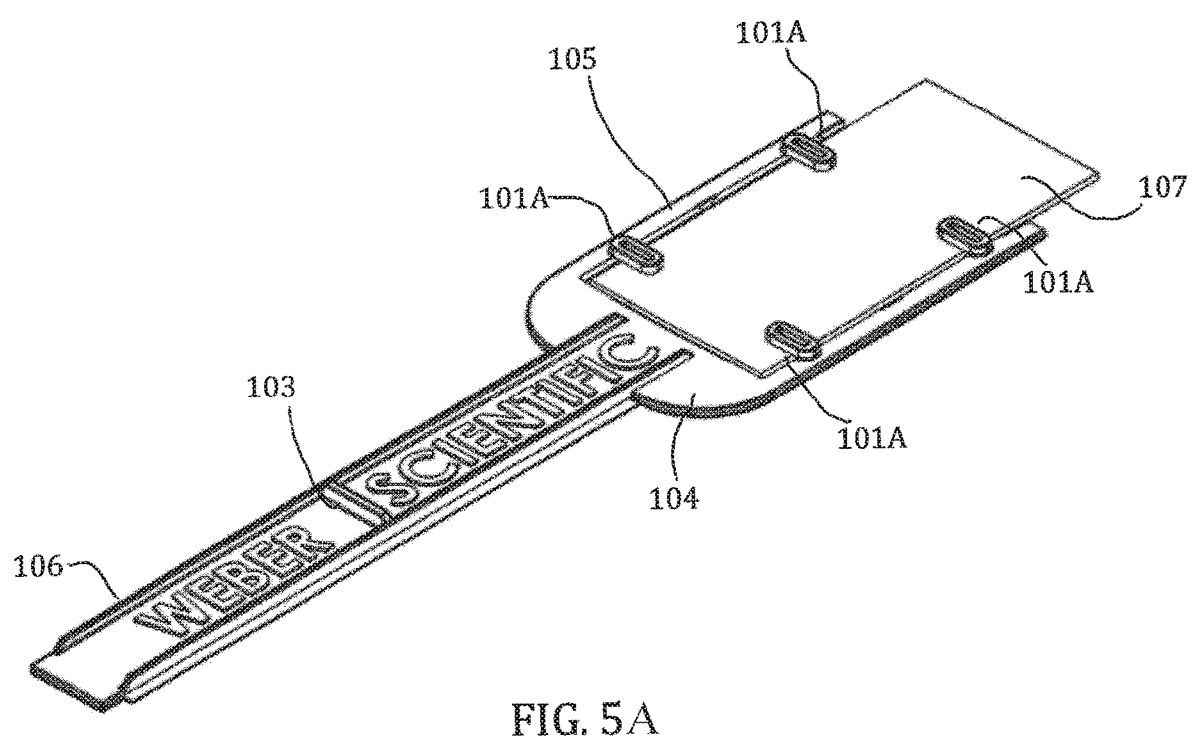
FIGS. 5A and 5B are an upper perspective view of the exemplary embodiment of FIG. 1, with a sample collector (e.g., sponge) loaded.
Figure 5B:
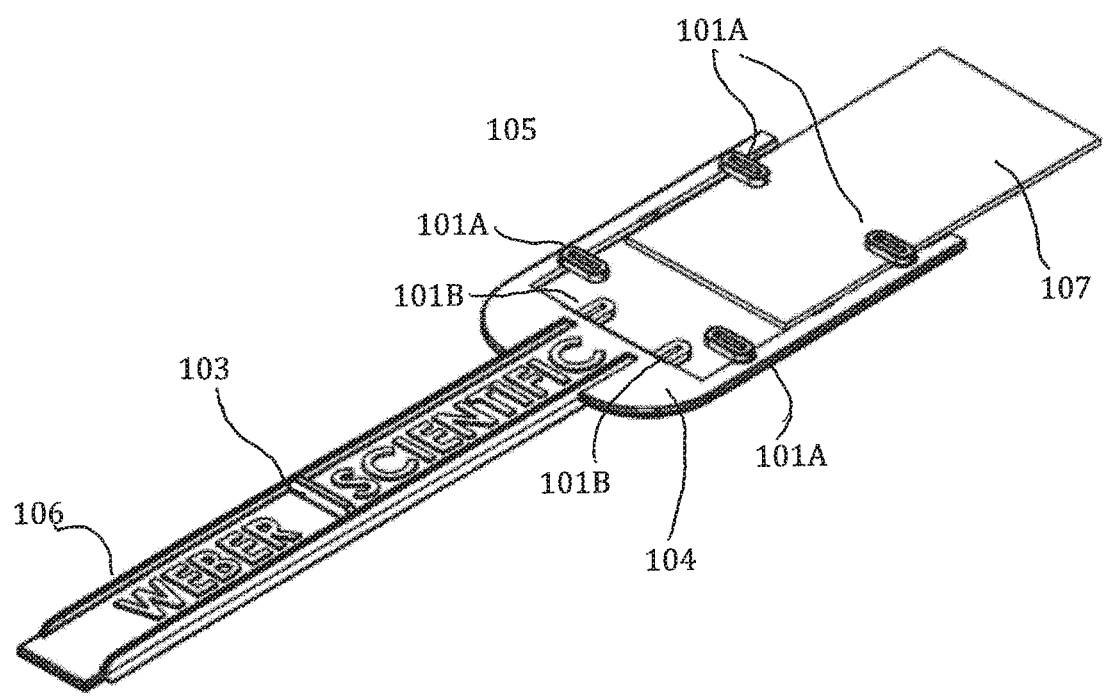

FIG. 5A shows the same device as in FIGS. 1 and 2, with the addition of removable sponge insert 107, shown fully inserted into frame 104. FIG. 5B shows sponge insert 107 only partially inserted, for purposes of illustration. Sponge insert 107 may be compressed-cellulose sponge, or is may be any other suitable compressed-sponge material known in the art of compressed-sponge manufacture. A suitable alternative material for some embodiments is polyvinyl alcohol (PVA) sponge, which is superior for some applications because it is biocompatible with most growing cells, and contains no inherent lint or fiber, and produces substantially less debris when cut.

In FIG. 5B the distance between the lower surface of cantilevers 101A, and the upper surface of cantilevers 101B is about 1 mm. The thickness of sponge insert 107 may be about the same or a bit less than about 1 mm. Thus, there is clearance for sponge insert 107 to slide into frame 104, with cantilevers 101A touching the top surface of 107, and cantilevers 101B touching the bottom surface, in a friction fit.

Figure 6:
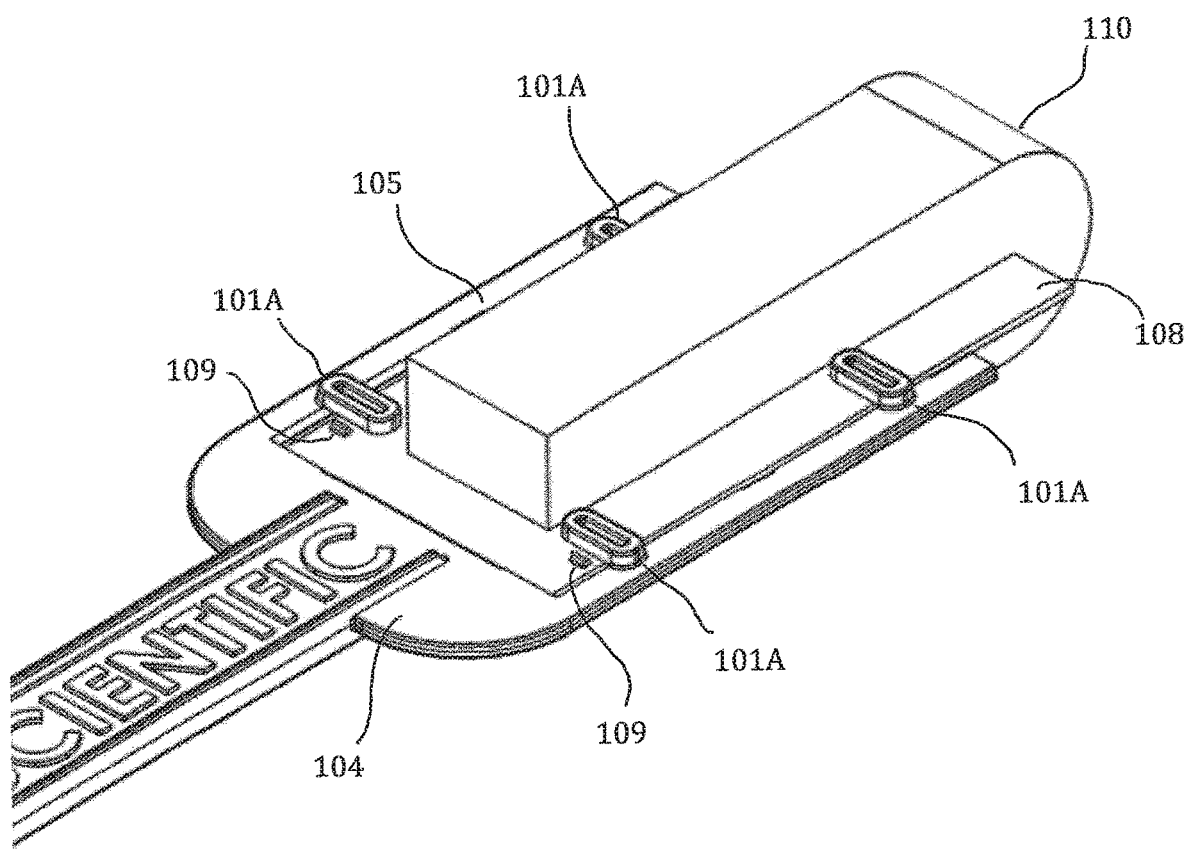
FIG. 6 is an upper perspective view of an additional exemplary embodiment of the present invention, with sliding plate feature.

FIG. 6 shows an alternate embodiment of the invention wherein a thin rigid base member or plate 108 is inserted into frame 104, with said plate/sheet being held in place in the same manner as the sponge insert of FIG. 1, that is, being held by friction force between cantilevers 101A and 101B. Glued for otherwise fastened upon plate 108 is rectangular collecting medium (e.g., sponge member) 110. Plate 108 is held in place by protrusions 109, which snap into place in contact with cantilevers 101A, thus adding additional stability to the structure. Collecting medium 110 is folded over the edge of plate 108, so that the collecting medium (e.g., sponge) exposes both major surfaces to the outside.

Figure 7:
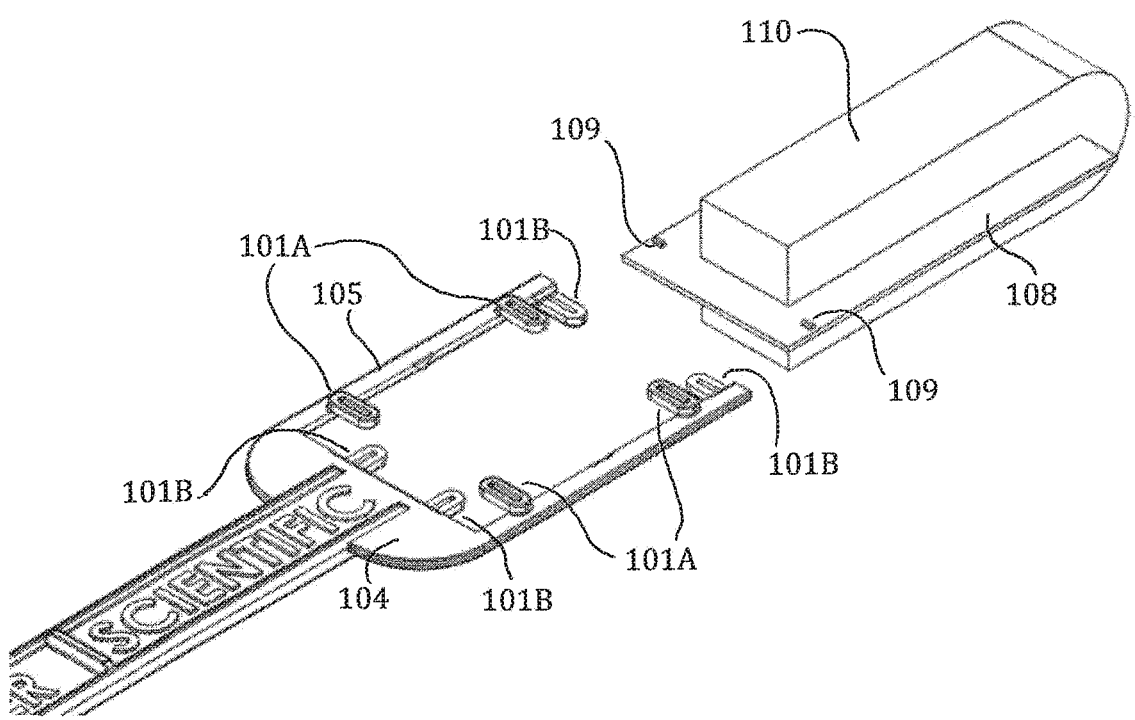
FIG. 7 is an exploded view of the exemplary embodiment of FIG. 6, with sliding plate feature.

FIG. 7 is a view of the device in FIG. 7 with plate member 108 removed from frame 104.

Figure 8:
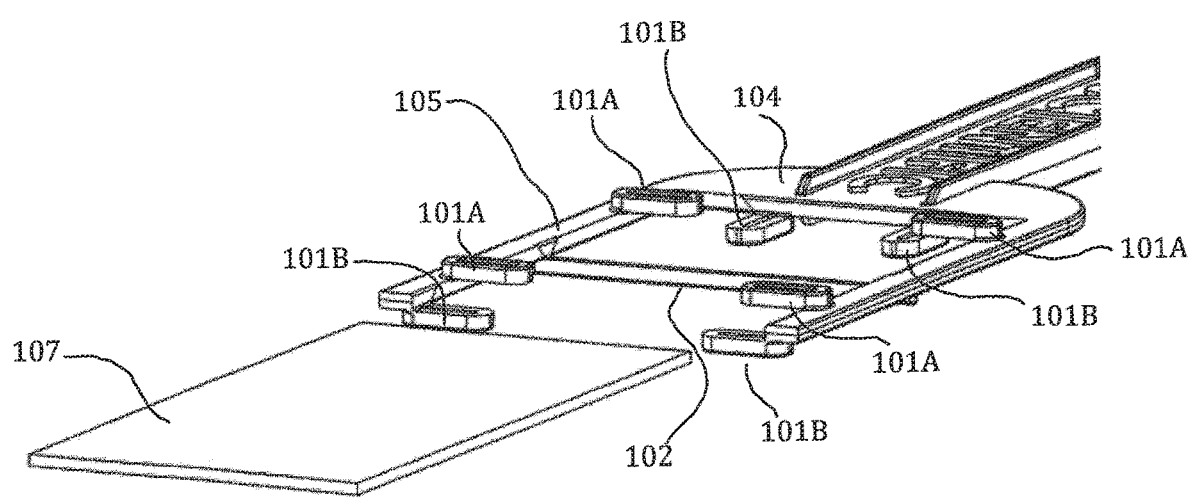
FIG. 8 is an exploded view of the exemplary embodiment of FIG. 7, with the compressed sponge just prior to insertion.

FIG. 8 is another perspective view of the device of FIG. 1, showing how sponge insert 107 is positioned just before insertion into frame 104. It can be seen that insert 107 slides beneath cantilevers 101A and above cantilevers 101B, and between tines 105.

Figure 9:
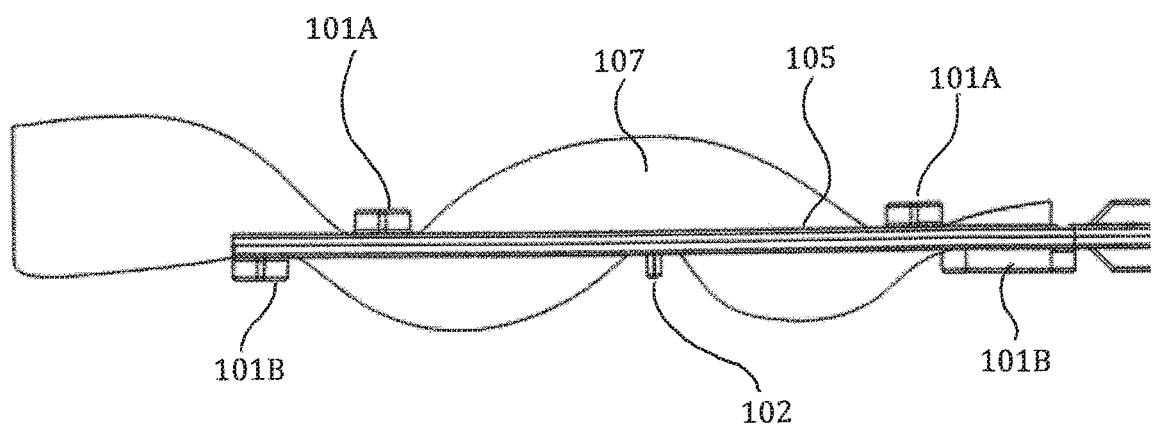
FIG. 9 is a side view of another exemplary embodiment the invention, with a sponge inserted and expanded.

FIG. 9 is a side view of the device of FIG. 1, showing sponge insert 107 inserted. Sponge insert 107 is as shown in previous figures. Tines 105 are a flat, rectangular prism of, e.g., 1 mm thickness. This was the form of the insert when dry.

FIG. 9 shows that when the sponge of FIG. 8 is exposed to water, the sponge expands, in this embodiment, from a thickness of about 1 mm to a thickness of about 8 mm. It can be seen that sponge 107 assumes a serpentine shape, expanding above and below the plane of frame 104. The water-expanded form of sponge 107 asserts forces against cantilevers 101A and 101B, and cross-brace 102, which act to hold sponge 107 into place. These forces prevent the sponge from slipping out of the frame while the sponge is swabbed on surfaces to be sampled. On the other hand, since there is no glue or other fixed connection between sponge 107 and frame 104, sponge 107 may be easily pulled out of frame 104 after the sampling task is done. The retaining means for the sponge is preferably designed to facilitate easy removal of a wet sponge from the frame by pulling, particularly by a user pulling with fingers exerting pressure through a plastic bag containing the device. The end result is that the sponge is separated from the handle and frame, with the swabbed sample material adsorbed or absorbed onto the sponge material. The separated handle may be removed from the bag, and the bag then sealed against contamination. The bag may then be sent for analysis at a laboratory.

Figure 10:
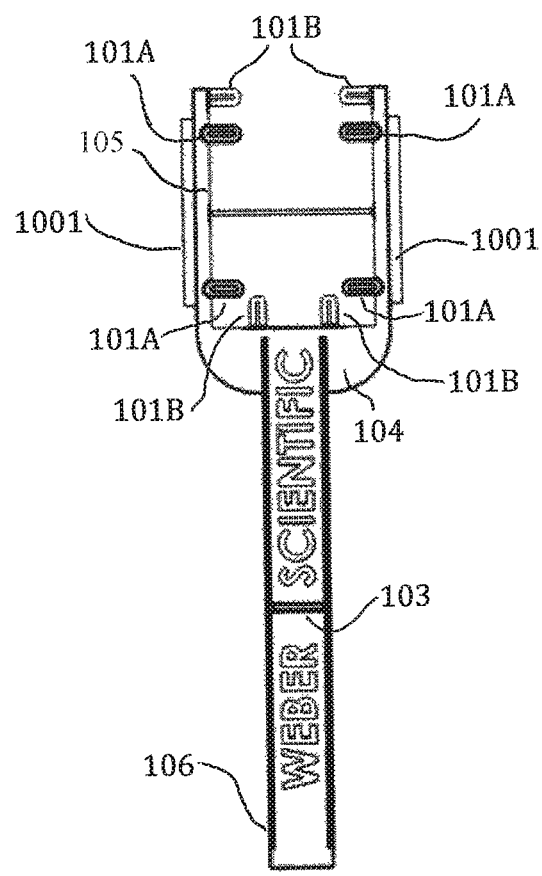
FIG. 10 is a top view of another exemplary embodiment the invention, showing how additional scraping blades may be placed on the tines.

An important feature of the embodiment of FIG. 9 is that cross-brace 102 is positioned such that it may scrape the surface being sampled while the sponge is being dragged across a surface being sample. This scraping will act to dislodge any biofilms on the surface, which might otherwise prevent bacteria from being taken up by the sponge. In other embodiments of the invention, other exposed surfaces of the frame, such as tines 105 may also be used as scrapers to disrupt biofilms. In one preferred embodiment, small, out-facing blades, made of a material the same as the tines, or different, may be incorporated into the tines to enhance scraping ability even more, as shown in FIG. 10. A feature of FIG. 9 is that the cross-brace member 102 is positioned so that scraping may occur with the surface being sampled, so that biofilm may be disrupted.

Sponge material suitable for the embodiment of FIG. 9 is typically supplied in sheets and cut to size. These are known as expanding, swelling, or pop-up sponges. Some of these are formed using dry cellulose sponges which are compressed under high pressure and heat. On contact with liquids they expand to their original size and have the same properties as an unpressed sponge from thence on. The liquid absorption factor of a compressed-sponge is up to 20 times its own weight. Suitable compressed-sponge material is described in the patent literature, for example in U.S. Pat. No. 3,634,183, which is incorporated by reference herein in its entirety.

FIG. 10 is a top view showing how additional scraping blades 1001 may be placed on tines 105. These blades might be, e.g., 0.5 mm plastic projections attached to tines 105, projecting outward from frame 104 in the same plane as the sponge insert.

A key advantage of a particular embodiment that can be seen in FIG. 9 is that sponge 107 projects open surface area both above and below the plane of frame. Therefore, once one side of sponge 107 has been swabbed against areas to be sampled, the user can simply rotate the whole device in her hand, so that the other side of sponge 107 may be used. Therefore, both sides of the sponge are available for sampling use, with no sponge surface being occluded by glue or other affixing means required to attached it to a handle. A further advantage is that one sponge may be used and removed, and then another sponge inserted into the same frame. Thus, the handle and frame may be re-used. If desired, the handle and frame may be machined out of materials that are not affected by autoclave temperatures, such as metal or high-temperature plastics. This permits sterile reuse of the device, avoiding wastage of the handle and frame materials, as may be the case with prior devices employing glue to attach the sponge.

Sometimes it may be desirable to have a swabbing surface with a special material that does not necessarily absorb water in the manner of a compressed-cellulose sponge. For these applications, a hybrid sponge insert may be used, comprising at least one layer of non-absorbent material flexibly glued or otherwise fastened to a layer of water-absorbent cellulose material. An insert of this layered material may be inserted into frame in the normal manner, with the non-absorbent material positioned outwardly, so that it is used for the actual swabbing task. Thus, the water-absorbing portion can perform its task of expanding and applying pressure which holds the insert against cantilevers 101A and 101B, thus holding the insert in place during swabbing. Meanwhile, the special, outer layer may be contacted with the surface to be sampled (e.g., to provide a scraper functionality).

Figure 11:
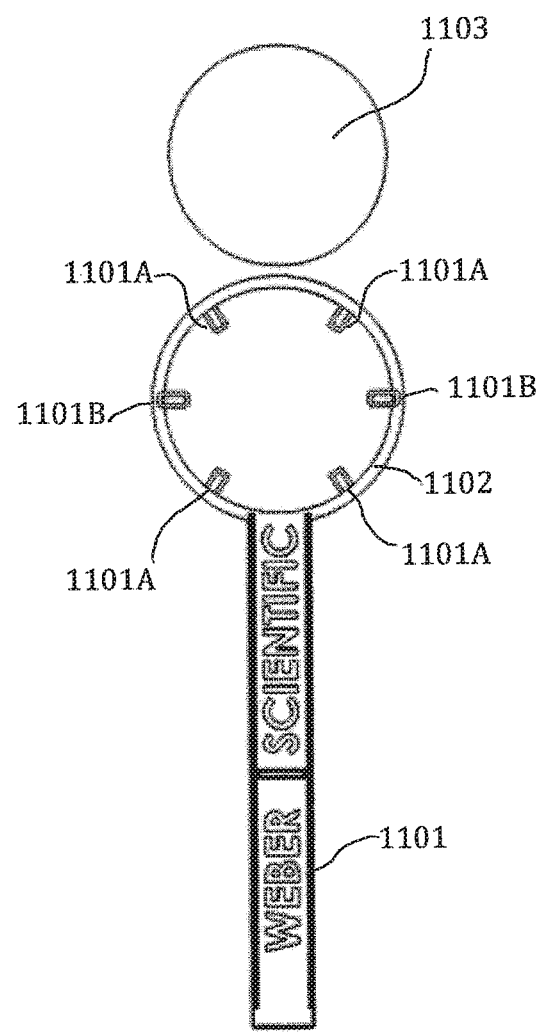
FIG. 11 is a top view of another exemplary embodiment the invention, showing an embodiment with a circular frame for holding the sponge insert.

FIG. 11 shows an embodiment wherein a frame comprises a handle 1101 attached to ring 1102, into which a circular disk of dry sampling material 1103 is inserted. The material is held in place by opposing cantilever sets 1101A and 1101B. When moisture is applied, said sampling material expands upward, and downward, and over the ring, locking it into place. After sampling, finger pressure may be applied to said material to cause it to flex and fall out of said ring.

Figure 12A:
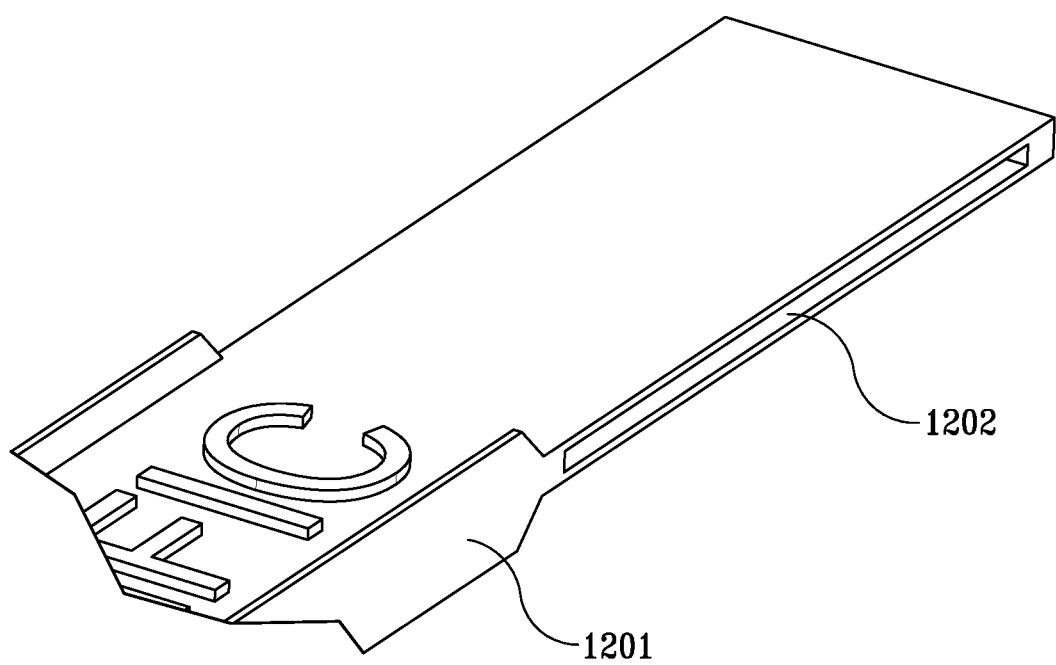
FIGS. 12A-12C show another exemplary embodiment the invention, employing a simple rod with slot for holding the sponge insert.
Figure 12B:
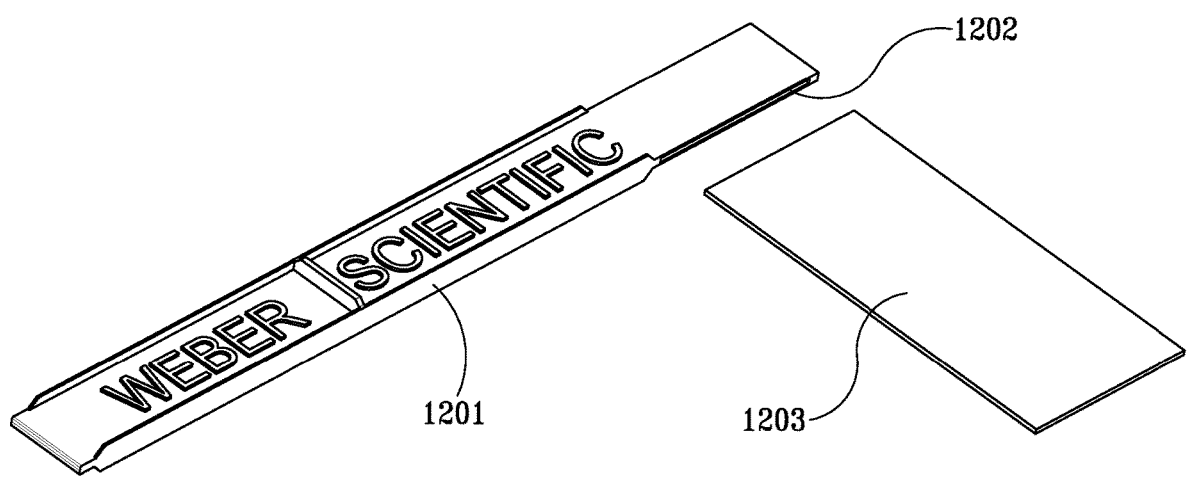
Figure 12C:
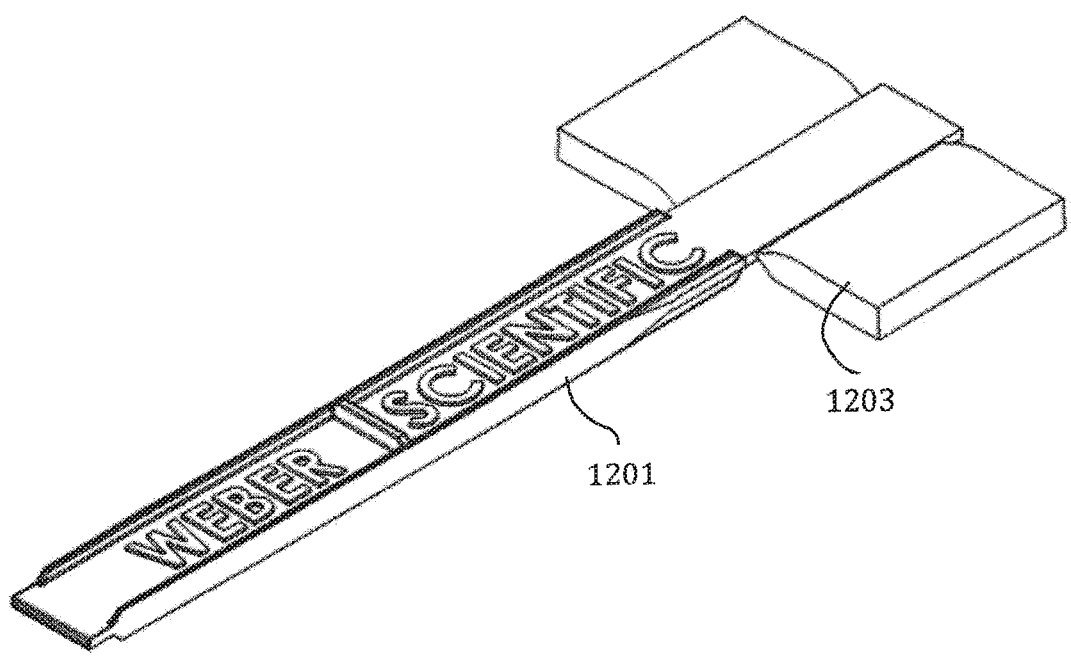

FIGS. 12A-12C show an embodiment where the handle and frame are integrated into a simple unit. FIG. 12A, shows a handle 1201 is a simple rod, with slot 1202 cut into one end. FIG. 12B shows a collecting member 1203, a rectangular prism of compressed sponge (e.g., 1 mm thick), being inserted through the slot 1202, to be positioned so that it is sticking out equally from both sides of the slot. Upon application of a liquid to said sponge, it expands as shown in FIG. 12C, and the expansion of sponge bulk on both sides of said slot tends to hold the sponge in place during surface sampling operations. Optionally present, but not shown in the example of FIGS. 12A-12C, is at least one scraping member (similar to the cross-brace member 102 shown in FIG. 2) on the outer surface of the handle member portion defining slot 1202 and configured to provide for scraping of a surface being sampled, to disrupt biofilm on the surface during sampling. The scraping member may be in-line with the handle axis or at some other orientation (e.g., orthogonal) with respect to the handle axis. Optionally, the end of the handle portion defining the slot is configured to function as a scraping member.

Figure 13A:
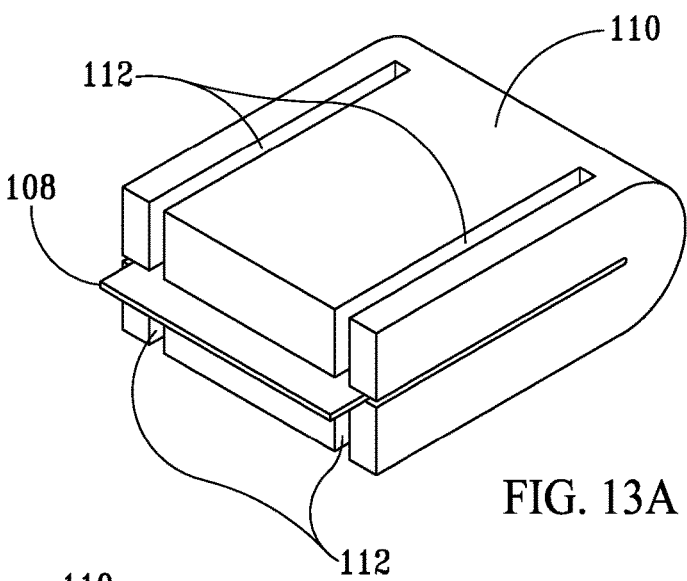
FIGS. 13A-13C show two additional exemplary collecting member embodiments (FIGS. 13A and 13B) of the invention, for use in combination with a sampling device 114 (FIG. 13C).
Figure 13B:
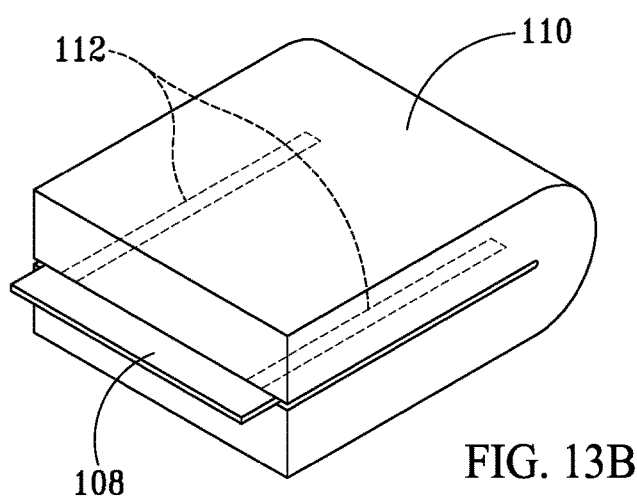
Figure 13C:
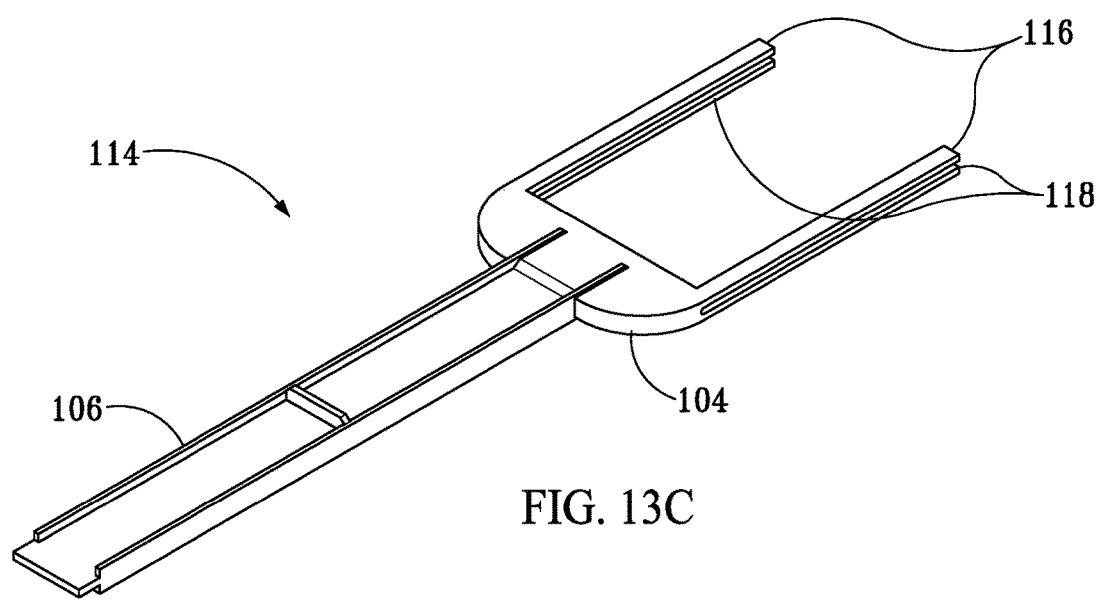

FIGS. 13A-13C show two additional exemplary collecting member embodiments (FIGS. 13A and 13B) of the invention, for use in combination with a sampling device 114 (FIG. 13C) comprising a handle 106, and a frame 104 having two tines extending from the frame 104 in a direction away from the handle 106, each tine being split or divided into an upper split tine portion 116 and a lower split tine portion 118. In both collecting member embodiments of FIGS. 13A and 13B, the colleting medium (e.g., sponge member) 110 is folded over and adhered to a base element or plate 108, except that there is no adherence of the collecting medium 110 to two non-adhered or exposed (e.g., slot-shaped) areas 112 on each of the upper and lower surfaces of the base element or plate 108. In FIG. 13A, slots in the adhered collecting medium 110 expose corresponding slot-shaped surface areas of the base element or plate 108 such that the non-adhered or exposed surfaces 112 are slidably received between the upper and lower split tine portions (116 and 118) of the sampling device 114. The collecting member of FIG. 13A provides an advantage that collecting material located at the side ends/edges of the collecting member can be used to sample from tight areas such as corners, without interference from the frame. In FIG. 13B, the folded adhered collecting medium 110 has no slots, and is rather not adhered at two non-adhered or exposed (e.g., slot-shaped areas) 112 on each of the upper and lower surfaces of the base element or plate 108 so that the non-adhered collecting medium 110 is sufficiently separable from the base element or plate 108 at these areas, such that the non-adhered or exposed surfaces 112 of the base element or plate 108 are slidably receivable between the split tines of the sampling device. As in the case of the collecting member of FIG. 13A, the collecting member of FIG. 13B provides an advantage that collecting material located at the side ends/edges of the collecting member can be used to sample from tight areas such as corners, without interference from the frame 104. Additionally, the collecting material of the collecting member of FIG. 13B when mounted to the frame 104, contacts the upper split tine portions 116 and a lower split tine portions 118 of the sampling device 114, to provide additional friction and facilitate retention of the collecting member to the sampling device 114. As in the other frame and collecting member embodiments disclosed herein, retention cantilevers 101A and/or 101B may be present on the upper split tine portions 116 and/or the lower split tine portions 118, and protrusions 109 or other complementary structures may be present on the non-adhered or exposed surfaces 112 of the collecting member 110 that snap into place in contact with cantilevers 101A and/or 101B, thus adding additional stability to the structure.

In particular embodiments, a scraper member is attached to at least one face, end or side of the collecting member (e.g., a rectangular sponge or the like), and the collecting member with the attached scraper member(s) is, in operation of the device, releasably mounted to the frame, which may or may not have a cross-brace member/scraper.

FIGS. 14A-14G show an additional exemplary collecting member embodiment of the invention, wherein the collecting member 128 has an attached scraper band 120.

Figure 14A:
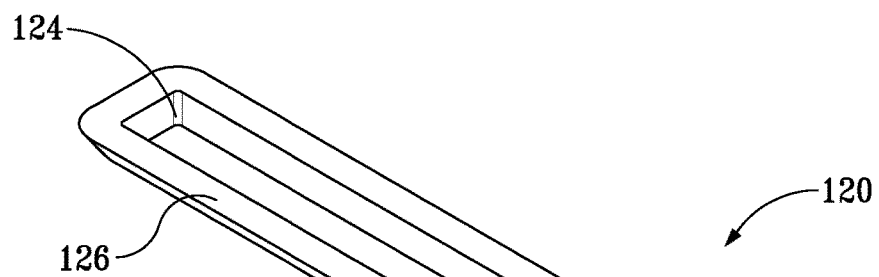
Figure 14B:
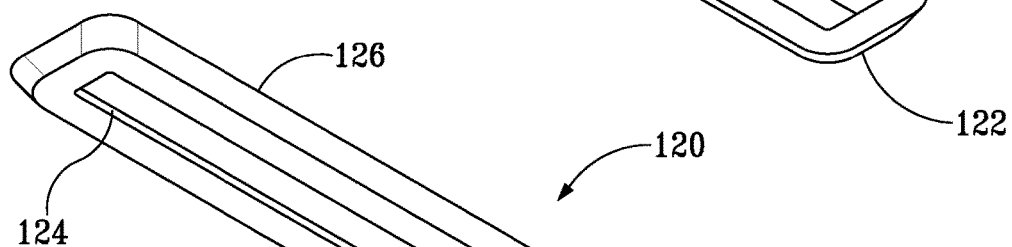
Figure 14C:
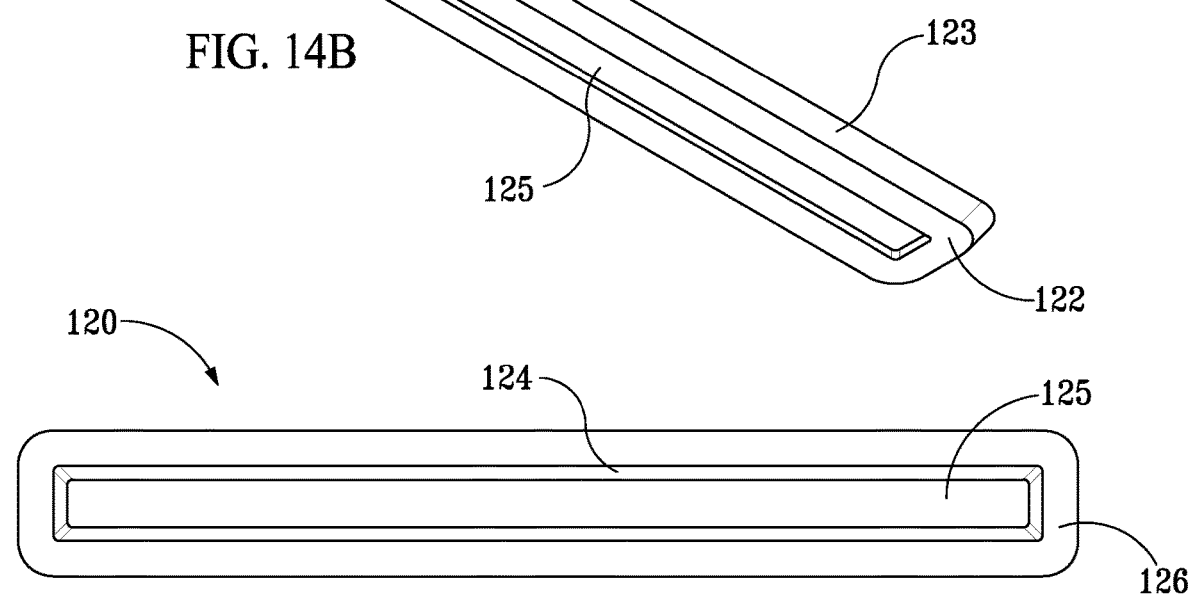
Figure 14D:
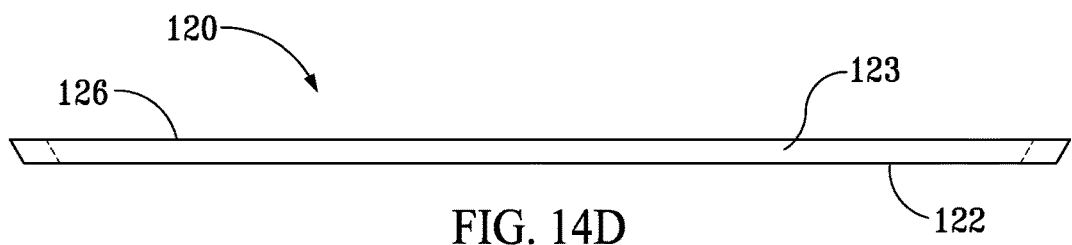

FIGS. 14A-14D show top perspective (14A), bottom perspective (14B), top (14C), and side (14D) views, respectively, of a scraper band 120 (e.g., formed of a resilient material) having outer top 122, outer bottom 126 and outer side 123 surfaces, and inner 124 surfaces extending (e.g., orthogonally, or at an angle) between the outer top 122 and the outer bottom 126 surfaces, at least portions of the outer surfaces (122, 126, and 123) being configured, in operation of the device, for contacting a surface to be sampled, and the inner surfaces 124 forming a slot 125 (e.g., angled slot as shown in FIGS. 14A-14C) into which a collecting member 128 is inserted and held in place by pinching pressure/compression between the inner surfaces 124 of the scraper band. With reference to FIGS. 14E-14G, for example, upon inserting the collecting member 128 into the slot 125 formed by inner surfaces 124 (see FIGS. 14E and 14F), and contacting the inserted collecting member 128 (e.g., sponge) with a liquid, the inserted collecting member 128 absorbs liquid and expands as shown in FIG. 14G and the expansion of collecting member 128 bulk on both sides of said slot 125 tends to hold the collecting member 128 (e.g., sponge) in place by compression or pinching pressure during surface sampling operations. The outer surfaces 122, 126, and 123 that span the outer surfaces of the collecting member 128 are planar or substantially planar, and may be configured to extend away from, or extend at an outward angle away from the collecting member 128 outer surface(s) to provide the scraping edge (e.g., as shown in FIGS. 14A-14G). The embodiment of FIGS. 14A-14G may further comprise a handle with a user gripping portion, the handle attached to a frame portion configured to retain the collecting member 128 and/or the band 120, to provide a sampling device for swabbing a surface and collecting a substance therefrom.

Figures 15A, 15B, 15C:
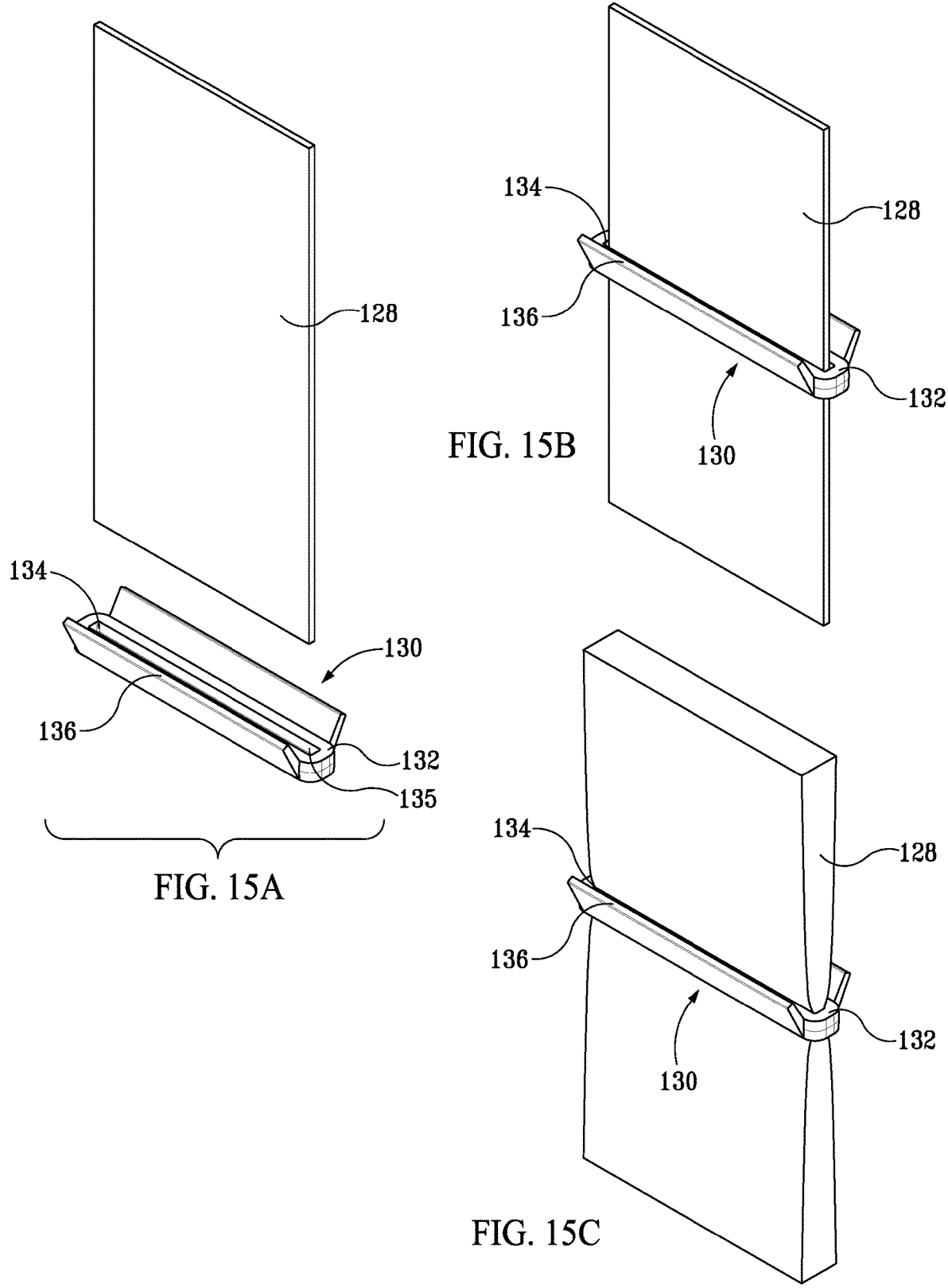
FIGS. 15A-15C show an additional exemplary collecting member embodiment of the invention, wherein the collecting member has an attached (or is combined with a) scraper band.

FIGS. 15A-15C show an additional exemplary collecting member embodiment of the invention, wherein the collecting member 128 has an attached scraper band 130. The scraper band 130 (e.g., formed of a resilient material) having outer top 132, outer bottom (not shown) and outer side 136 surfaces, and inner 134 surfaces extending (e.g., orthogonally, or at an angle) between the outer top 132 and the outer bottom (not shown) surfaces, at least portions of the outer surfaces (132, 136, and outer bottom) being configured, in operation of the device, for contacting a surface to be sampled, and the inner surfaces 134 forming a slot 135 (e.g., that may be an angled slot as shown in the scraper band embodiment of FIGS. 14A-14C) into which a collecting member 128 is inserted and held in place by pinching pressure/compression between the inner surfaces 134 of the scraper band 130. With reference to FIGS. 15A-15C, for example, upon inserting the collecting member 128 into the slot 135 formed by inner surfaces 134, and contacting the inserted collecting member 128 (e.g., sponge) with a liquid, the inserted collecting member 128 absorbs liquid and expands as shown in FIG. 15C, and the expansion of collecting member 128 bulk on both sides of said slot 135 tends to hold the collecting member 128 (e.g., sponge) in place by compression or pinching pressure during surface sampling operations. The outer surfaces 122, 126, and 123 that span the outer surfaces of the collecting member 128 are planar or substantially planar, and may be configured to extend away from, or extend at an outward angle away from the collecting member 128 outer surface(s) to provide the scraping edge (e.g., as shown in FIGS. 14A-14G). The embodiment of FIGS. 15A-15C may further comprise a handle with a user gripping portion, the handle attached to a frame portion configured to retain the collecting member 128 and/or the band 130, to provide a sampling device for swabbing a surface and collecting a substance therefrom.

FIGS. 16A-16C show an additional exemplary collecting member embodiment of the invention, wherein the collecting member 128 has an attached scraper band 140. The scraper band 140 (e.g., formed of a resilient material) having outer top 146, outer bottom 142 and outer side 143 surfaces, and inner 144 surfaces extending (e.g., orthogonally, or at an angle) between the outer top 146 and the outer bottom 142 surfaces, at least portions of the outer surfaces (146, 142, and 143) being configured, in operation of the device, for contacting a surface to be sampled, and the inner surfaces 144 forming a slot 145 (e.g., angled slot as shown in FIGS. 14A-14C) into which a collecting member 128 is inserted and held in place by pinching pressure/compression between the inner surfaces 144 of the scraper band 140. With reference to FIGS. 16A-16C, for example, upon inserting the collecting member 128 into the slot 145 formed by inner surfaces 144, and contacting the inserted collecting member 128 (e.g., sponge) with a liquid, the inserted collecting member 128 absorbs liquid and expands as shown in FIG. 16C, and the expansion of collecting member 128 bulk on both sides of said slot 145 tends to hold the collecting member 128 (e.g., sponge) in place by compression or pinching pressure during surface sampling operations. The outer surfaces 146, 142, and 143 that span the outer surfaces of the collecting member 128 are planar or substantially planar, and may, for example, be configured to be substantially horizontal with the sampling device, the non-wetted or wetted collecting member, and/or the surface being sampled, as shown in the embodiment of FIGS. 16A-16C. The embodiment of FIGS. 16A-16C may further comprise a handle with a user gripping portion, the handle attached to a frame portion configured to retain the collecting member 128 and/or the band 140, to provide a sampling device for swabbing a surface and collecting a substance therefrom.

Figure 17A:
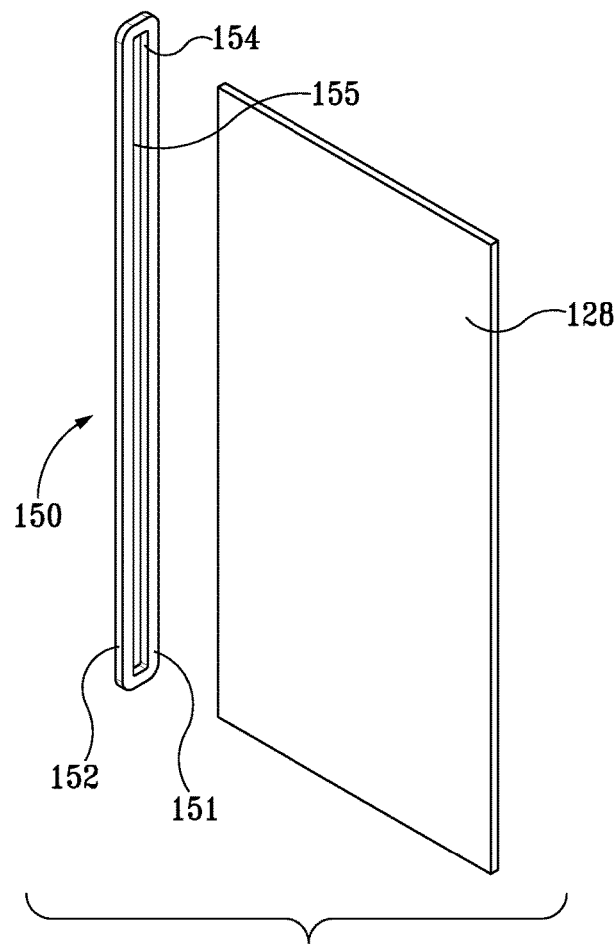
FIGS. 17A-17C show a further exemplary collecting member embodiment of the invention, wherein the collecting member has an attached (or is combined with a) scraper band that is orthogonally positioned on the collecting member relative to the positioning/direction of the scraper band embodiment of FIGS. 16A-16C on the collecting member.
Figure 17B:
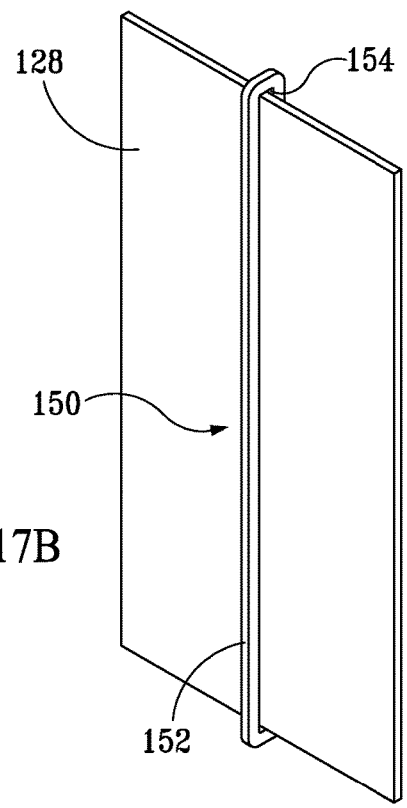
Figure 17C:
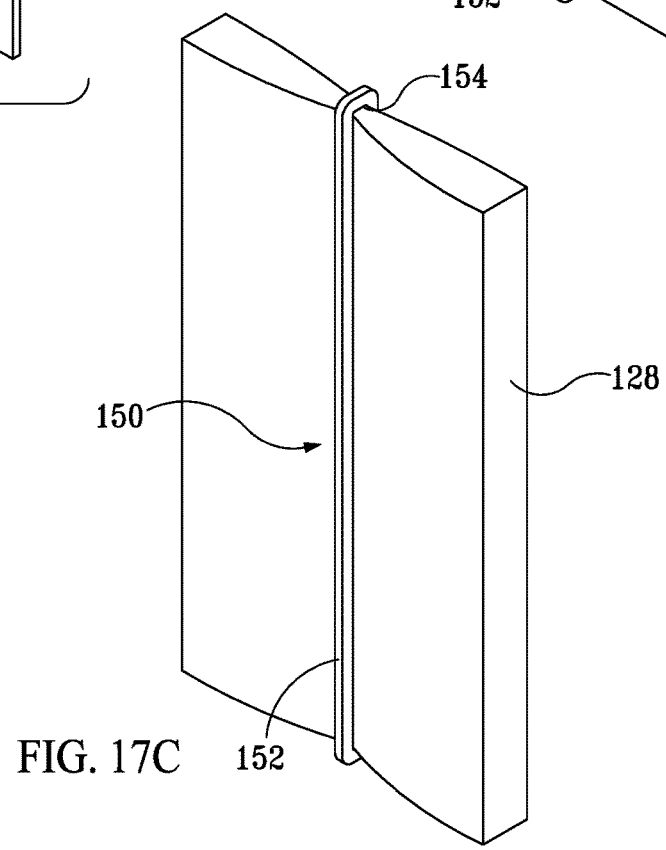

FIGS. 17A-17C show a further exemplary collecting member embodiment of the invention, wherein the collecting member 128 has an attached scraper band 150 that is orthogonally positioned on the collecting member 128 relative to the positioning/direction of the scraper band 140 embodiment of FIGS. 16A-16C on the collecting member 128. The scraper band 150 (e.g., formed of a resilient material) having outer top 151, outer bottom (not shown) and outer side 152 surfaces, and inner 154 surfaces extending (e.g., orthogonally, or at an angle) between the outer top 151 and the outer bottom (not shown) surfaces, at least portions of the outer surfaces (151, 152, and outer bottom) being configured, in operation of the device, for contacting a surface to be sampled, and the inner surfaces 154 forming a slot 155 (e.g., angled slot as shown in FIGS. 14A-14C) into which a collecting member 128 is inserted and held in place by pinching pressure/compression between the inner surfaces 154 of the scraper band 150. With reference to FIGS. 17A-17C, for example, upon inserting the collecting member 128 into the slot 155 formed by inner surfaces 154, and contacting the inserted collecting member 128 (e.g., sponge) with a liquid, the inserted collecting member 128 absorbs liquid and expands as shown in FIG. 17C, and the expansion of collecting member 128 bulk on both sides of said slot 155 tends to hold the collecting member 128 (e.g., sponge) in place by compression or pinching pressure during surface sampling operations. The outer surfaces 151, 152, and outer bottom that span the outer surfaces of the collecting member 128 are planar or substantially planar, and may, for example, be configured to be substantially horizontal with the sampling device, the non-wetted or wetted collecting member, and/or the surface being sampled, as shown in the embodiment of FIGS. 17A-17C. The embodiment of FIGS. 17A-17C may further comprise a handle with a user gripping portion, the handle attached to a frame portion configured to retain the collecting member 128 and/or the band 150, to provide a sampling device for swabbing a surface and collecting a substance therefrom.

Figure 18:
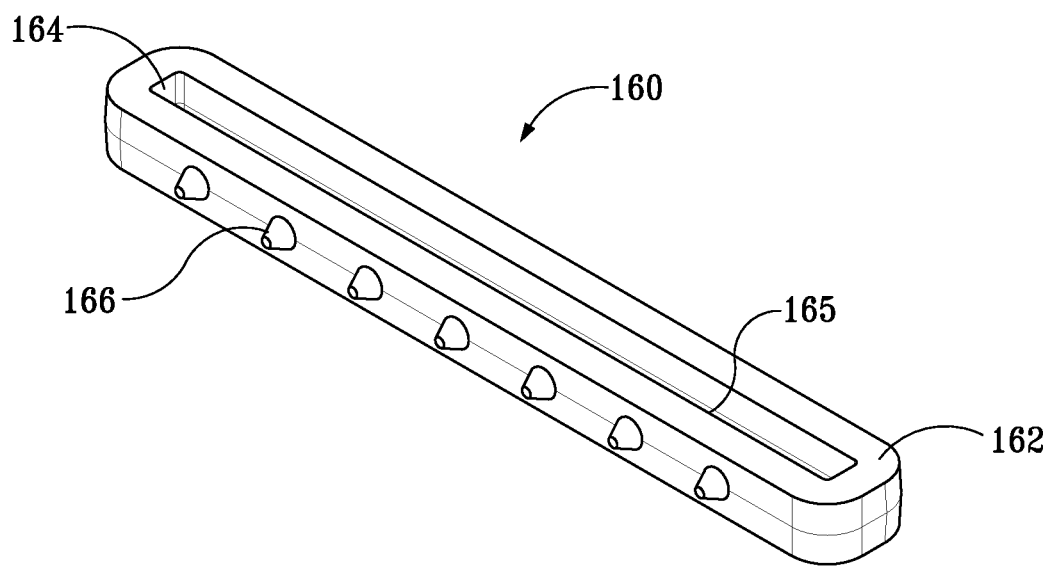
FIG. 18 shows a yet further exemplary collecting member embodiment of the invention, wherein the collecting member (not shown) has an attached (or is combined with a) scraper band having raised portions to provide one or more scraping edges.

FIG. 18 shows a yet further exemplary collecting member embodiment of the invention, wherein the collecting member 128 (not shown) has an attached scraper band 160. The scraper band 160 (e.g., formed of a resilient material) having outer top 162, outer bottom (not shown) and outer side 166 surfaces, and inner 164 surfaces extending (e.g., orthogonally, or at an angle) between the outer top 162 and the outer bottom (not shown) surfaces, at least portions of the outer surfaces (162, 166, and outer bottom) being configured, in operation of the device, for contacting a surface to be sampled, and the inner surfaces 164 forming a slot 165 (e.g., angled slot as shown in FIGS. 14A-14C) into which a collecting member 128 is inserted and held in place by pinching pressure/compression between the inner surfaces 164 of the scraper band 160. For example, upon inserting the collecting a member 128 into the slot 165 formed by inner surfaces 164, and contacting the inserted collecting member 128 (e.g., sponge) with a liquid, the inserted collecting member 128 absorbs liquid and expansion of the collecting member 128 bulk on both sides of said slot 165 tends to hold the collecting member 128 (e.g., sponge) in place by compression or pinching pressure during surface sampling operations. The outer surfaces 162, 166, and outer bottom that span the outer surfaces of the collecting member 128 are planar or substantially planar, and may, for example, be configured to be substantially horizontal with the sampling device, the non-wetted or wetted collecting member, and/or the surface being sampled. At least one of the outer surfaces 162, 166, and outer bottom that span the outer surfaces of the collecting member 128 may additionally comprise one or more raised portions to provide one or more scraping edges as shown in the embodiment of FIG. 18. The embodiment of FIG. 18 may further comprise a handle with a user gripping portion, the handle attached to a frame portion configured to retain the collecting member 128 and/or the band 160, to provide a sampling device for swabbing a surface and collecting a substance therefrom.

The scraper bands of the exemplary embodiments described herein can be continuous bands configured to provide a resilient slot for insertion and retention of the collecting member/media. Alternatively, the scraper bands may be configured to be discontinuous, comprising one or more joints, such that the scraper band can be positioned and joined around a collecting member to form a resilient slot retaining the collecting member.

The scraper bands may be comprised of essentially any resilient material or combinations thereof (e.g., polymers, metallic, etc.) that can be rendered sterile.

In particular aspects, the outer surface of the scraper band is, or comprises an abrasive or is textured (e.g., grit, mesh, spun fibers/wools and the like), or comprises ridge(s), protrusions, or the like, to facilitate scraping and dislodging of material during sampling. In particular embodiments, a spun polypropylene fiber (e.g., Scotch-Brite™, and the like) is attached to the outer surface of the scraper band or to the collecting member.

In yet further embodiments, a scraping member is provided by attaching an abrasive or texture material to at least one surface (e.g., upper lower, side, end) of a collecting member (e.g., attaching a strip or patch of abrasive material, grit, mesh, spun fibers/wools, etc.).

The foregoing embodiments are intended to illustrate preferred embodiments of the claimed invention, and do not limit the intended scope.

Disclosed are components that can be used to perform the disclosed devices and methods. These and other components are disclosed herein, and it is understood that when combinations, subsets, interactions, groups, etc. of these components are disclosed that while specific reference of each various individual and collective combinations and permutations of these may not be explicitly disclosed, each is specifically contemplated and described herein, for all devices and methods. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:

1. A device for swabbing a surface and collecting a substance therefrom, comprising:
   a handle having a user gripping portion or end and a frame end;
   a frame connected to or integral with the handle at the frame end and having upper and lower frame surfaces, the frame defining an inner framed or partially framed area; and
   cantilever retention members positioned on the frame, each extending from the frame in an inward direction at least partially over or under the inner framed or partially framed area, wherein at least one of the cantilever retention members extends at least partially over the inner framed or partially framed area, and at least one of the cantilever retention members extends under the inner framed or partially framed area, and wherein the frame and the cantilever retention members are configured to cooperatively receive and frictionally retain, by application of force in a direction orthogonal to the inward direction of the cantilever retention members in operation of the device, a releasably mountable collecting member between the at least one cantilever retention member extending at least partially over, and the at least one cantilever retention member extending at least partially under the inner framed or partially framed area, within the inner, framed or partially framed area.

2. The device of claim 1, wherein at least one of the cantilever retention members is positioned on each of the upper and the lower frame surfaces.

3. The device of claim 1, wherein the frame is circular, or is rectangular having at least two sides, a closed frame end proximate to the handle and an open frame end distal to the handle, in each case configured to facilitate, in operation of the device, receipt of a collecting member.

4. The device of claim 3, wherein the frame is rectangular and comprises two tines extending from the frame end of the handle, each tine having at least one of the cantilever retention members and configured, in operation of the device, to receive and frictionally retain a collecting member.

5. The device of claim 4, further comprising at least one cross-brace member extending between and/or connecting the tines, wherein the cross-brace member is positioned and configured to provide for scraping of a surface being sampled, to disrupt biofilm or other surface substance during sampling.

6. The device of claim 4, wherein each tine is longitudinally split or divided into an upper split tine portion and a lower split tine portion to provide the cantilever retention members and configured, in operation of the device, to receive and frictionally retain a portion of a collecting member.

7. The device of claim 1, further comprising a mounted and/or frictionally retained collecting member.

8. The device of claim 7, wherein the collecting member comprises an expandable collecting material or medium that undergoes expansion upon absorption of a liquid, and wherein the frame and the cantilever retention members are configured to receive and retain the expandable collecting material or medium by pinching or gripping pressure after absorption of the liquid.

9. The device of claim 8, wherein the collecting member comprises a non-expandable or substantially non-expandable base element or plate attached to or integral with the collecting material or medium that undergoes expansion upon absorption of a liquid, and wherein the frame and cantilever members are configured to frictionally retain a portion of the non-expandable or substantially non-expandable base element or plate.

10. The device of claim 9, wherein the non-expandable or substantially non-expandable base element or plate comprises protrusions or other structures that cooperatively contact the frame and/or the cantilever members to provide friction or stability for retaining the collecting member.

11. The device of claim 8, wherein the collecting material or medium that undergoes expansion upon absorption of the liquid comprises at least one sampling medium selected from the group consisting of: sponge, polyurethane, cotton, cellulose, and microfiber.

12. The device of claim 7, wherein the collecting member comprises: a non-expandable or substantially non-expandable base element or plate having upper and lower surfaces and an edge, the base element or plate fixedly attached to or integral with a collecting material that undergoes expansion upon absorption of liquid, the collecting material sized to cover at least a majority portion of the upper and lower surfaces of the base element or plate, and folded over the edge thereof.

13. The device of claim 12, wherein the base element or plate is rectangular or square, having upper and lower surfaces to which the collecting material is attached, and four sides or edges comprising the edge covered by the folded-over collecting material, an opposite edge free of collecting material, and two side edges, and wherein a portion of the upper and/or lower surface of the plate is either free of the collecting material or not attached to the collecting material, to provide an accessible surface area configured for mounting the collecting member to a receiving frame of a sampling device.

14. The device of claim 12, wherein the collecting material that undergoes expansion upon absorption of liquid, or a portion thereof, is configured to have a narrow and/or angled portion to facilitate surface sampling access in tight or restricted areas of a surface.

15. The device of claim 13, further comprising protrusions or other structures on the accessible surface area configured, in operation of the collecting member, to provide friction or stability for retaining the collecting member to a receiving frame.

16. The device of claim 12, further comprising a scraper member configured, in operation of the collecting member, for contacting a surface to be sampled.

17. The device of claim 16. wherein the scraper member comprises a scraper band formed of a resilient material and having an outer and an inner surface, the inner surface forming a slot configured to retain the collecting member by pinching pressure or compression between portions of the inner surface, and the outer surface comprising a scraping edge configured, in operation of the collecting member, for contacting and scraping a surface to be sampled.

18. The device of claim 17, wherein the outer surface of the scraper band comprises one or more portions configured to extend away from, or extend at an outward angle away from the collecting member to provide the scraping edge.

19. The device of claim 12, further comprising a handle with a user gripping portion, the handle attached to a frame portion configured to retain the collecting member, to provide a sampling device for swabbing a surface and collecting a substance therefrom.

* * * * *